(12) United States Patent
Brown et al.

(10) Patent No.: US 8,945,009 B2
(45) Date of Patent: *Feb. 3, 2015

(54) REMOTE HEALTH MONITORING SYSTEM

(75) Inventors: Stephen J. Brown, Woodside, CA (US); Gowthaman Gunabushanam, Hyderabad (IN)

(73) Assignee: Robert Bosch Heathcare Systems, Inc., Palo Alto, CA (US)

( * ) Notice: Subject to any disclaimer, the term of this patent is extended or adjusted under 35 U.S.C. 154(b) by 870 days.

This patent is subject to a terminal disclaimer.

(21) Appl. No.: 12/137,660

(22) Filed: Jun. 12, 2008

(65) Prior Publication Data

US 2008/0269571 A1    Oct. 30, 2008

Related U.S. Application Data

(63) Continuation of application No. 10/840,945, filed on May 7, 2004, now Pat. No. 7,399,276.

(60) Provisional application No. 60/469,453, filed on May 8, 2003.

(51) Int. Cl.
*A61B 5/00* (2006.01)
*G06F 19/00* (2011.01)

(52) U.S. Cl.
CPC .......... *A61B 5/0022* (2013.01); *G06F 19/3418* (2013.01); *Y10S 128/92* (2013.01); *G06F 19/3493* (2013.01)
USPC ................ 600/301; 600/300; 705/2; 128/920

(58) Field of Classification Search
USPC .................. 128/903–905, 920–925; 705/2–4; 340/573.1–576; 600/300–301
See application file for complete search history.

(56) References Cited

U.S. PATENT DOCUMENTS

| 3,426,150 A | 2/1969 | Tygart |
| 3,566,365 A | 2/1971 | Rawson et al. |
| 3,566,370 A | 2/1971 | Worthington, Jr. et al. |

(Continued)

FOREIGN PATENT DOCUMENTS

| EP | 0286456 | 10/1988 |
| EP | 0320749 | 6/1989 |

(Continued)

OTHER PUBLICATIONS

+5V Powered Isolated RS-232 Drivers/Receivers Maxim Integrated Products.

(Continued)

*Primary Examiner* — William Thomson
*Assistant Examiner* — Bobby Soriano
(74) *Attorney, Agent, or Firm* — Maginot Moore & Beck LLP

(57) ABSTRACT

The invention relates generally to remote health monitoring systems, as applied to the field of public health surveillance. In particular, it relates to a multi-user remote health monitoring system that is capable of reliably identifying and collecting data from frontline healthcare providers, laboratory and hospital information systems, patients and healthy individuals in a number of ways, with a view to aid in the field of public health. The system can also be used to query and collect additional information regarding specifics pertaining to the health of the individuals, and for patient tracking, monitoring, and the collection of individual data.

11 Claims, 17 Drawing Sheets

(56) References Cited

U.S. PATENT DOCUMENTS

| | | |
|---|---|---|
| 3,581,072 A | 5/1971 | Nymeyer |
| 3,768,014 A | 10/1973 | Smith et al. |
| 3,811,116 A | 5/1974 | Takeuchi et al. |
| 3,883,235 A | 5/1975 | Lynn et al. |
| 3,910,257 A | 10/1975 | Fletcher et al. |
| 3,920,005 A | 11/1975 | Gombrich et al. |
| 3,996,928 A | 12/1976 | Marx |
| 4,004,577 A | 1/1977 | Sarnoff |
| 4,051,522 A | 9/1977 | Healy et al. |
| 4,060,915 A | 12/1977 | Conway |
| 4,130,881 A | 12/1978 | Haessler et al. |
| 4,150,284 A | 4/1979 | Trenkler et al. |
| 4,151,407 A | 4/1979 | McBride et al. |
| 4,151,831 A | 5/1979 | Lester |
| 4,173,971 A | 11/1979 | Karz |
| 4,216,462 A | 8/1980 | McGrath et al. |
| 4,227,526 A | 10/1980 | Goss |
| 4,253,521 A | 3/1981 | Savage |
| 4,259,548 A | 3/1981 | Fahey et al. |
| 4,270,547 A | 6/1981 | Steffen et al. |
| 4,296,756 A | 10/1981 | Dunning et al. |
| 4,347,568 A | 8/1982 | Giguere et al. |
| 4,347,851 A | 9/1982 | Jundanian |
| 4,360,345 A | 11/1982 | Hon |
| 4,412,287 A | 10/1983 | Braddock, III |
| 4,417,306 A | 11/1983 | Citron et al. |
| 4,422,081 A | 12/1983 | Woods |
| 4,428,733 A | 1/1984 | Kumar-Misir |
| 4,449,536 A | 5/1984 | Weaver |
| 4,465,077 A | 8/1984 | Schneider |
| 4,473,884 A | 9/1984 | Behl |
| 4,518,361 A | 5/1985 | Conway |
| 4,519,398 A | 5/1985 | Lisiecki et al. |
| 4,531,527 A | 7/1985 | Reinhold, Jr. |
| 4,546,436 A | 10/1985 | Schneider et al. |
| 4,566,461 A | 1/1986 | Lubell et al. |
| 4,576,578 A | 3/1986 | Parker et al. |
| 4,592,546 A | 6/1986 | Fascenda et al. |
| 4,627,445 A | 12/1986 | Garcia |
| 4,674,652 A | 6/1987 | Aten et al. |
| 4,686,624 A | 8/1987 | Blum et al. |
| 4,694,490 A | 9/1987 | Harvey et al. |
| 4,695,954 A | 9/1987 | Rose et al. |
| 4,712,562 A | 12/1987 | Ohayon et al. |
| 4,722,349 A | 2/1988 | Baumberg |
| 4,729,381 A | 3/1988 | Harada et al. |
| 4,730,253 A | 3/1988 | Gordon |
| 4,731,726 A | 3/1988 | Allen, III |
| 4,738,451 A | 4/1988 | Logg |
| 4,768,229 A | 8/1988 | Benjamin et al. |
| 4,779,199 A | 10/1988 | Yoneda et al. |
| 4,782,511 A | 11/1988 | Nemec et al. |
| 4,789,928 A | 12/1988 | Fujisaki |
| 4,796,639 A | 1/1989 | Snow et al. |
| 4,799,156 A | 1/1989 | Shavit et al. |
| 4,799,199 A | 1/1989 | Scales, III et al. |
| 4,803,625 A | 2/1989 | Fu et al. |
| 4,835,372 A | 5/1989 | Gombrich et al. |
| 4,838,275 A | 6/1989 | Lee |
| 4,846,797 A | 7/1989 | Howson et al. |
| 4,853,521 A | 8/1989 | Claeys et al. |
| 4,858,354 A | 8/1989 | Gettler |
| 4,858,617 A | 8/1989 | Sanders |
| 4,890,621 A | 1/1990 | Hakky |
| 4,894,777 A | 1/1990 | Negishi et al. |
| 4,897,869 A | 1/1990 | Takahashi |
| 4,899,839 A | 2/1990 | Dessertine et al. |
| 4,903,201 A | 2/1990 | Wagner |
| 4,907,973 A | 3/1990 | Hon |
| 4,916,441 A | 4/1990 | Gombrich |
| 4,931,934 A | 6/1990 | Snyder |
| 4,933,873 A | 6/1990 | Kaufman et al. |
| 4,933,876 A | 6/1990 | Markoff et al. |
| 4,950,246 A | 8/1990 | Muller |
| 4,950,264 A | 8/1990 | Osborn, III |
| 4,953,552 A | 9/1990 | DeMarzo |
| 4,958,632 A | 9/1990 | Duggan |
| 4,958,641 A | 9/1990 | Digby et al. |
| 4,967,756 A | 11/1990 | Hewitt |
| 4,977,899 A | 12/1990 | Digby et al. |
| 4,978,303 A | 12/1990 | Lampbell |
| 4,978,335 A | 12/1990 | Arthur, III |
| 4,979,509 A | 12/1990 | Hakky |
| 5,007,429 A | 4/1991 | Treatch et al. |
| 5,009,645 A | 4/1991 | Silver et al. |
| 5,016,172 A | 5/1991 | Dessertine |
| 5,019,974 A | 5/1991 | Beckers |
| 5,024,225 A | 6/1991 | Fang |
| 5,025,374 A | 6/1991 | Roizen et al. |
| 5,034,807 A | 7/1991 | Von Kohorn |
| 5,035,625 A | 7/1991 | Munson et al. |
| 5,036,462 A | 7/1991 | Kaufman et al. |
| 5,049,487 A | 9/1991 | Phillips et al. |
| 5,050,612 A | 9/1991 | Matsumura |
| 5,056,059 A | 10/1991 | Tivig et al. |
| 5,059,394 A | 10/1991 | Phillips et al. |
| 5,065,315 A | 11/1991 | Garcia |
| 5,068,536 A | 11/1991 | Rosenthal |
| 5,074,317 A | 12/1991 | Bondell et al. |
| 5,077,476 A | 12/1991 | Rosenthal |
| 5,077,665 A | 12/1991 | Silverman et al. |
| 5,095,798 A | 3/1992 | Okada et al. |
| 5,104,380 A | 4/1992 | Holman et al. |
| 5,109,414 A | 4/1992 | Harvey et al. |
| 5,109,974 A | 5/1992 | Beer et al. |
| 5,111,396 A | 5/1992 | Mills et al. |
| 5,111,817 A | 5/1992 | Clark et al. |
| 5,111,818 A | 5/1992 | Suzuki et al. |
| 5,120,230 A | 6/1992 | Clark et al. |
| 5,120,421 A | 6/1992 | Glass et al. |
| 5,128,552 A | 7/1992 | Fang et al. |
| 5,128,752 A | 7/1992 | Von Kohorn |
| 5,134,391 A | 7/1992 | Okada |
| 5,142,358 A | 8/1992 | Jason |
| 5,142,484 A | 8/1992 | Kaufman et al. |
| 5,143,378 A | 9/1992 | Joel |
| 5,171,977 A | 12/1992 | Morrison |
| 5,176,502 A | 1/1993 | Sanderson et al. |
| 5,182,707 A | 1/1993 | Cooper et al. |
| 5,204,670 A | 4/1993 | Stinton |
| 5,219,322 A | 6/1993 | Weathers |
| 5,222,020 A | 6/1993 | Takeda |
| 5,226,895 A | 7/1993 | Harris |
| 5,227,874 A | 7/1993 | Von Kohorn |
| 5,228,450 A | 7/1993 | Sellers |
| 5,230,629 A | 7/1993 | Buschke |
| 5,231,990 A | 8/1993 | Gauglitz |
| 5,243,515 A | 9/1993 | Lee |
| 5,249,044 A | 9/1993 | Von Kohorn |
| 5,251,126 A | 10/1993 | Kahn et al. |
| 5,261,401 A | 11/1993 | Baker et al. |
| 5,262,943 A | 11/1993 | Thibado et al. |
| 5,265,888 A | 11/1993 | Yamamoto et al. |
| 5,266,179 A | 11/1993 | Nankai et al. |
| 5,275,159 A | 1/1994 | Griebel |
| 5,282,950 A | 2/1994 | Dietze et al. |
| 5,295,491 A | 3/1994 | Gevins |
| 5,299,121 A | 3/1994 | Brill et al. |
| 5,301,105 A | 4/1994 | Cummings, Jr. |
| 5,304,112 A | 4/1994 | Mrklas et al. |
| 5,304,468 A | 4/1994 | Phillips et al. |
| 5,307,263 A | 4/1994 | Brown |
| 5,309,919 A | 5/1994 | Snell et al. |
| 5,321,009 A | 6/1994 | Baeder et al. |
| 5,325,288 A | 6/1994 | Satou |
| 5,329,459 A | 7/1994 | Kaufman et al. |
| 5,329,608 A | 7/1994 | Bocchieri et al. |
| 5,331,549 A | 7/1994 | Crawford, Jr. |
| 5,333,981 A | 8/1994 | Pronovost et al. |
| 5,335,338 A | 8/1994 | Proesel |
| 5,339,821 A | 8/1994 | Fujimoto |
| 5,341,291 A | 8/1994 | Roizen et al. |
| 5,343,239 A | 8/1994 | Lappington et al. |
| 5,344,324 A | 9/1994 | O'Donnell et al. |

(56) References Cited

U.S. PATENT DOCUMENTS

| | | |
|---|---|---|
| 5,357,427 A | 10/1994 | Langen et al. |
| 5,366,896 A | 11/1994 | Margrey et al. |
| 5,368,562 A | 11/1994 | Blomquist et al. |
| 5,371,687 A | 12/1994 | Holmes, II et al. |
| 5,375,604 A | 12/1994 | Kelly et al. |
| 5,377,100 A | 12/1994 | Pope et al. |
| 5,390,238 A | 2/1995 | Kirk et al. |
| 5,399,821 A | 3/1995 | Inagaki et al. |
| 5,410,471 A | 4/1995 | Alyfuku et al. |
| 5,410,474 A | 4/1995 | Fox |
| 5,429,140 A | 7/1995 | Burdea et al. |
| 5,431,690 A | 7/1995 | Schaldach et al. |
| 5,431,691 A | 7/1995 | Snell et al. |
| 5,434,611 A | 7/1995 | Tamura |
| 5,438,607 A | 8/1995 | Przygoda, Jr. et al. |
| 5,438,983 A | 8/1995 | Falcon |
| 5,441,047 A | 8/1995 | David et al. |
| 5,449,334 A | 9/1995 | Kingsbury |
| 5,454,721 A | 10/1995 | Kuch |
| 5,454,722 A | 10/1995 | Holland et al. |
| 5,456,606 A | 10/1995 | McIntyre |
| 5,456,692 A | 10/1995 | Smith, Jr. et al. |
| 5,458,123 A | 10/1995 | Unger |
| 5,467,269 A | 11/1995 | Flaten |
| 5,471,039 A | 11/1995 | Irwin, Jr. et al. |
| 5,471,382 A | 11/1995 | Tallman et al. |
| 5,483,276 A | 1/1996 | Brooks et al. |
| 5,488,412 A | 1/1996 | Majeti et al. |
| 5,488,423 A | 1/1996 | Walkingshaw et al. |
| 5,501,231 A | 3/1996 | Kaish |
| 5,502,636 A | 3/1996 | Clarke |
| 5,502,726 A | 3/1996 | Fischer |
| 5,504,519 A | 4/1996 | Remillard |
| 5,517,405 A | 5/1996 | McAndrew et al. |
| 5,518,001 A | 5/1996 | Snell |
| 5,519,058 A | 5/1996 | Gonick et al. |
| 5,519,433 A | 5/1996 | Lappington et al. |
| 5,523,232 A | 6/1996 | Sechler |
| 5,536,249 A | 7/1996 | Castellano et al. |
| 5,542,420 A | 8/1996 | Goldman et al. |
| 5,544,649 A | 8/1996 | David et al. |
| 5,546,943 A | 8/1996 | Gould |
| 5,549,117 A | 8/1996 | Tacklind et al. |
| 5,550,575 A | 8/1996 | West et al. |
| 5,553,609 A | 9/1996 | Chen et al. |
| 5,558,638 A | 9/1996 | Evers et al. |
| 5,564,429 A | 10/1996 | Bornn et al. |
| 5,569,212 A | 10/1996 | Brown |
| 5,572,421 A | 11/1996 | Altman et al. |
| 5,572,646 A | 11/1996 | Kawai et al. |
| 5,574,828 A | 11/1996 | Hayward et al. |
| 5,576,952 A | 11/1996 | Stutman et al. |
| 5,583,758 A | 12/1996 | McIlroy et al. |
| 5,590,648 A | 1/1997 | Mitchell et al. |
| 5,593,349 A | 1/1997 | Miguel et al. |
| 5,593,390 A | 1/1997 | Castellano et al. |
| 5,594,637 A | 1/1997 | Eisenberg et al. |
| 5,596,994 A | 1/1997 | Bro |
| 5,597,307 A | 1/1997 | Redford et al. |
| 5,601,435 A | 2/1997 | Quy |
| 5,613,495 A | 3/1997 | Mills et al. |
| 5,619,991 A * | 4/1997 | Sloane ............... 600/300 |
| 5,624,265 A | 4/1997 | Redford et al. |
| 5,628,309 A | 5/1997 | Brown |
| 5,629,981 A | 5/1997 | Nerlikar |
| 5,631,844 A | 5/1997 | Margrey et al. |
| 5,633,910 A | 5/1997 | Cohen |
| 5,635,532 A | 6/1997 | Samid |
| 5,640,569 A | 6/1997 | Miller et al. |
| 5,640,953 A | 6/1997 | Bishop et al. |
| 5,642,731 A | 7/1997 | Kehr |
| 5,642,936 A | 7/1997 | Evans |
| 5,651,363 A | 7/1997 | Kaufman et al. |
| 5,651,775 A | 7/1997 | Walker et al. |
| 5,659,691 A | 8/1997 | Durward et al. |
| 5,666,487 A | 9/1997 | Goodman et al. |
| 5,670,711 A | 9/1997 | Detournay et al. |
| 5,675,635 A | 10/1997 | Vos et al. |
| 5,678,562 A | 10/1997 | Sellers |
| 5,678,571 A | 10/1997 | Brown |
| 5,679,075 A | 10/1997 | Forrest et al. |
| 5,680,590 A | 10/1997 | Parti |
| 5,680,866 A | 10/1997 | Kangas et al. |
| 5,687,322 A | 11/1997 | Deaton et al. |
| 5,687,717 A | 11/1997 | Halpern et al. |
| 5,687,734 A | 11/1997 | Dempsey et al. |
| 5,689,652 A | 11/1997 | Lupien et al. |
| 5,692,906 A | 12/1997 | Corder |
| 5,704,364 A | 1/1998 | Saltzstein et al. |
| 5,704,366 A | 1/1998 | Tacklind et al. |
| 5,704,902 A | 1/1998 | Vandenbelt et al. |
| 5,704,922 A | 1/1998 | Brown |
| 5,710,178 A | 1/1998 | Samid |
| 5,710,918 A | 1/1998 | Lagarde et al. |
| 5,711,297 A | 1/1998 | Iliff |
| 5,714,319 A | 2/1998 | Joutel et al. |
| 5,715,451 A | 2/1998 | Marlin |
| 5,715,823 A | 2/1998 | Wood et al. |
| 5,717,739 A | 2/1998 | Dyer et al. |
| 5,717,913 A | 2/1998 | Driscoll |
| 5,720,733 A | 2/1998 | Brown |
| 5,722,418 A | 3/1998 | Bro |
| 5,727,153 A | 3/1998 | Powell |
| 5,730,124 A | 3/1998 | Yamauchi |
| 5,730,654 A | 3/1998 | Brown |
| 5,732,696 A | 3/1998 | Rapoport et al. |
| 5,732,709 A | 3/1998 | Tacklind et al. |
| 5,734,413 A | 3/1998 | Lappington et al. |
| 5,749,083 A | 5/1998 | Koda et al. |
| 5,752,234 A | 5/1998 | Withers |
| 5,754,740 A | 5/1998 | Fukuoka et al. |
| 5,760,771 A | 6/1998 | Blonder et al. |
| 5,772,585 A | 6/1998 | Lavin et al. |
| 5,778,882 A | 7/1998 | Raymond et al. |
| 5,782,814 A | 7/1998 | Brown et al. |
| 5,785,650 A | 7/1998 | Akasaka et al. |
| 5,787,295 A | 7/1998 | Nakao |
| 5,791,342 A | 8/1998 | Woodard |
| 5,792,117 A | 8/1998 | Brown |
| 5,793,969 A | 8/1998 | Kamentsky et al. |
| 5,794,219 A | 8/1998 | Brown |
| 5,794,251 A | 8/1998 | Watanabe et al. |
| 5,796,393 A | 8/1998 | MacNaughton et al. |
| 5,799,318 A | 8/1998 | Cardinal et al. |
| 5,800,458 A | 9/1998 | Wingrove |
| 5,802,494 A | 9/1998 | Kuno |
| 5,802,534 A | 9/1998 | Hatayama et al. |
| 5,806,057 A | 9/1998 | Gormley et al. |
| 5,810,747 A | 9/1998 | Brudny et al. |
| 5,819,735 A | 10/1998 | Mansfield et al. |
| 5,822,544 A | 10/1998 | Chaco et al. |
| 5,822,715 A | 10/1998 | Worthington et al. |
| 5,825,283 A | 10/1998 | Camhi |
| 5,827,180 A | 10/1998 | Goodman |
| 5,828,943 A | 10/1998 | Brown |
| 5,832,448 A | 11/1998 | Brown |
| 5,835,896 A | 11/1998 | Fisher et al. |
| 5,840,020 A | 11/1998 | Heinonen et al. |
| 5,842,976 A | 12/1998 | Williamson |
| 5,868,669 A | 2/1999 | Iliff |
| 5,868,683 A | 2/1999 | Protopapas et al. |
| 5,875,432 A | 2/1999 | Sehr |
| 5,879,163 A | 3/1999 | Brown et al. |
| 5,882,338 A | 3/1999 | Gray |
| 5,887,133 A | 3/1999 | Brown et al. |
| 5,893,077 A | 4/1999 | Griffin |
| 5,893,098 A | 4/1999 | Peters et al. |
| 5,897,493 A | 4/1999 | Brown |
| 5,899,855 A | 5/1999 | Brown |
| 5,911,687 A | 6/1999 | Sato et al. |
| 5,913,310 A | 6/1999 | Brown |
| 5,918,603 A | 7/1999 | Brown |
| 5,920,477 A | 7/1999 | Hofberg et al. |
| 5,933,136 A | 8/1999 | Brown |

(56) References Cited

U.S. PATENT DOCUMENTS

| | | |
|---|---|---|
| 5,935,060 A | 8/1999 | Iliff |
| 5,940,801 A | 8/1999 | Brown |
| 5,941,829 A | 8/1999 | Saltzstein et al. |
| 5,945,651 A | 8/1999 | Chorosinski et al. |
| 5,951,300 A | 9/1999 | Brown |
| 5,954,641 A | 9/1999 | Kehr et al. |
| 5,956,501 A | 9/1999 | Brown |
| 5,960,403 A | 9/1999 | Brown |
| 5,961,446 A | 10/1999 | Beller et al. |
| 5,966,526 A | 10/1999 | Yokoi |
| 5,971,855 A | 10/1999 | Ng |
| 5,971,922 A | 10/1999 | Arita et al. |
| 5,983,003 A | 11/1999 | Lection et al. |
| 5,983,217 A | 11/1999 | Khosravi-Sichani et al. |
| 5,987,471 A | 11/1999 | Bodine et al. |
| 5,995,969 A | 11/1999 | Lee et al. |
| 5,997,476 A | 12/1999 | Brown |
| 5,997,502 A | 12/1999 | Reilly et al. |
| 6,001,065 A | 12/1999 | DeVito |
| 6,022,315 A | 2/2000 | Iliff |
| 6,022,615 A | 2/2000 | Rettenbacher |
| 6,023,686 A | 2/2000 | Brown |
| 6,024,281 A | 2/2000 | Shepley |
| 6,029,138 A | 2/2000 | Khorasani et al. |
| 6,032,119 A | 2/2000 | Brown et al. |
| 6,035,328 A | 3/2000 | Soukal |
| 6,046,761 A | 4/2000 | Echerer |
| 6,049,794 A | 4/2000 | Jacobs et al. |
| 6,050,940 A | 4/2000 | Braun et al. |
| 6,055,314 A | 4/2000 | Spies et al. |
| 6,055,487 A | 4/2000 | Margery et al. |
| 6,055,506 A | 4/2000 | Frasca, Jr. |
| 6,057,758 A | 5/2000 | Dempsey et al. |
| 6,068,615 A | 5/2000 | Brown et al. |
| 6,095,985 A | 8/2000 | Raymond et al. |
| 6,101,478 A | 8/2000 | Brown |
| 6,110,148 A | 8/2000 | Brown et al. |
| 6,113,578 A | 9/2000 | Brown |
| 6,138,145 A | 10/2000 | Kawanaka |
| 6,144,837 A | 11/2000 | Quy |
| 6,151,586 A | 11/2000 | Brown |
| 6,161,095 A | 12/2000 | Brown |
| 6,167,362 A | 12/2000 | Brown et al. |
| 6,167,386 A | 12/2000 | Brown |
| 6,168,563 B1 | 1/2001 | Brown |
| 6,177,940 B1 | 1/2001 | Bond et al. |
| 6,186,145 B1 | 2/2001 | Brown |
| 6,189,029 B1 | 2/2001 | Fuerst |
| D439,242 S | 3/2001 | Brown et al. |
| 6,210,272 B1 | 4/2001 | Brown |
| 6,221,012 B1 | 4/2001 | Maschke et al. |
| 6,231,519 B1 | 5/2001 | Blants et al. |
| 6,233,539 B1 | 5/2001 | Brown |
| 6,238,337 B1 * | 5/2001 | Kambhatla et al. ............ 600/300 |
| 6,240,393 B1 | 5/2001 | Brown |
| 6,248,065 B1 | 6/2001 | Brown |
| 6,260,022 B1 | 7/2001 | Brown |
| 6,270,455 B1 | 8/2001 | Brown |
| 6,270,456 B1 | 8/2001 | Iliff |
| 6,334,778 B1 | 1/2002 | Brown |
| 6,352,523 B1 | 3/2002 | Brown et al. |
| 6,368,273 B1 | 4/2002 | Brown |
| 6,370,513 B1 | 4/2002 | Kolawa et al. |
| 6,375,469 B1 | 4/2002 | Brown |
| 6,379,301 B1 | 4/2002 | Worthington et al. |
| 6,381,577 B1 | 4/2002 | Brown |
| 6,436,036 B1 | 8/2002 | Miller-Kovach et al. |
| 6,454,705 B1 | 9/2002 | Cosentino et al. |
| 6,513,532 B2 | 2/2003 | Mault et al. |
| 7,024,370 B2 * | 4/2006 | Epler et al. ..................... 705/3 |
| 7,034,691 B1 * | 4/2006 | Rapaport et al. ............ 340/573.1 |
| 7,427,920 B2 * | 9/2008 | Martin et al. ............... 340/573.1 |
| 7,840,421 B2 * | 11/2010 | Gerntholtz ..................... 705/3 |
| 2002/0019748 A1 | 2/2002 | Brown |
| 2003/0009239 A1 * | 1/2003 | Lombardo et al. ............ 700/30 |
| 2003/0163351 A1 * | 8/2003 | Brown et al. ............... 600/300 |
| 2003/0204130 A1 | 10/2003 | Colston et al. |
| 2004/0106855 A1 | 6/2004 | Brown |
| 2004/0107116 A1 | 6/2004 | Brown |
| 2004/0117207 A1 | 6/2004 | Brown |
| 2004/0117208 A1 | 6/2004 | Brown |
| 2004/0117209 A1 | 6/2004 | Brown |
| 2004/0117210 A1 | 6/2004 | Brown |
| 2004/0199056 A1 * | 10/2004 | Husemann et al. ........... 600/300 |

FOREIGN PATENT DOCUMENTS

| | | |
|---|---|---|
| EP | 370599 | 5/1990 |
| EP | 0461910 | 12/1991 |
| EP | 508912 | 10/1992 |
| EP | 526166 | 2/1993 |
| EP | 0558975 | 9/1993 |
| EP | 0653718 | 5/1995 |
| EP | 676709 | 10/1995 |
| EP | 680727 | 11/1995 |
| EP | 761160 | 3/1997 |
| EP | 08131551 | 12/1997 |
| EP | 0251520 | 1/1998 |
| GB | 2218831 | 11/1989 |
| GB | 2225637 | 6/1990 |
| JP | 54005785 | 1/1979 |
| JP | 54146633 | 11/1979 |
| JP | 62226278 | 10/1987 |
| JP | 5155024 | 6/1993 |
| JP | 5266002 | 10/1993 |
| JP | 199540709596 | 4/1995 |
| WO | WO-8501667 | 4/1985 |
| WO | WO-90/00367 | 1/1990 |
| WO | WO-9109374 | 6/1991 |
| WO | WO-93/01489 | 1/1993 |
| WO | WO-9302622 | 2/1993 |
| WO | WO-9416774 | 8/1994 |
| WO | WO-95/09386 | 4/1995 |
| WO | WO-95/20199 | 7/1995 |
| WO | WO-9522131 | 8/1995 |
| WO | WO-9529447 | 11/1995 |
| WO | WO-96/07908 | 3/1996 |
| WO | WO-96/25877 | 8/1996 |
| WO | WO-9636923 | 11/1996 |
| WO | WO-97/08605 | 3/1997 |
| WO | WO-97/12544 | 4/1997 |
| WO | WO-9737738 | 10/1997 |
| WO | WO-98/16895 | 4/1998 |
| WO | WO-9831275 | 7/1998 |
| WO | WO-9839933 | 9/1998 |

OTHER PUBLICATIONS

Adilman; "Videogames: Knowing the Score"; Creative Computing; v9; p. 224(5); Dec. 1983; Dialog: File 148, Acc# 01891055.

AdOptimizer—Ad Management Software for Websites, Newsbytes, pNEW10040041, Oct. 4, 1996.

Albisser, A.M. "Intelligent Instrumentation in Diabetic Management", CRC Critical Reviews in Biomedical Engineering, vol. 17, No. 1, pp. 1-24.

Anonymous, "Health Hero Network, Inc. Receives First-Ever FDA Clearance for Connecting Medical Devices to Internet", PR Newswire, (Dec. 2, 1993), 3 pages.

Antique Collector , Putting the Lot on the Net, vol. 66, Issue 9, p. 26, Downloaded from Corporate Resource Net, Nov./Dec. 1995.

Bai, "Design of home healthcare network", IEEE 1997 pp. 1657-1658.

Billiard, A., et al. "Telematic Transmission of Computerized Blood Glucose Profiles for IDDm Patients", Diabetes Care, (Feb. 1991), vol. 14, No. 2, pp. 130-134.

Blood Glucose Monitors, Portable Health Device, (1998), vol. 17(9), pp. 253-271.

Bower, "Brain Clues to Energy-efficient Learning", Science News, (Apr. 1992), v. 141; p215(1); Dialog: File 647, Acct# 12123949.

Brenman et al.; "Interaction of Nitric Oxide Synthase with the Postsynaptic Density Protein PSD-95 and α1-Syntrophin Mediated by PDZ Domains"; Cell; vol. 84, pp. 757-767, Mar. 8, 1996; Ref: XP-002104701.

(56) References Cited

OTHER PUBLICATIONS

Bruce, "Health Hero Network CEO, CNNfn", Digital Jam, (Dec. 1, 1999), 3.
Bruce, et al., "The Effects of Sympathetic Nervous System Activation and Psychological Stress . . . "; Diabetologia; 35(9); 1992; 835-843; Dialog: File 5, Acc#9629427. (9 pages).
Brunetti, P., et al., "A Simulation Study on a Self-Turning Portable Controller of Blood Glucose", The International Journal of Artificial Organs, (1993), vol. 16, No. 16, pp. 51-57.
Caprihan, A., et al., "A Simple Microcomputer for Biomedical Signal Processing", IECI '78 Annual Conference Proceedings on Industrial Applications of Microprocessors, (Mar. 20, 1978), 18-23.
Cathay Pacific Airways—USA receives more than 1,300 bids during first five days of CyberAuction; Business Wire, Oct. 18, 1995, p. 10181119.
Cathay Pacific Airways—USA to Hold First-Ever Internet CyberAuction; CyberTravelers Can Bid for 50 Business Class Round Trips to Hong Kong—No Minimum Bid; Business Wire; p. 9261084; Sep. 26, 1995; Dialog: File 148, Acc#08167091.
CD-ROM Mavericks: Proprietary TV-Based Players, Byte Guide to CD-ROM, pp. 100-105.
Central Fetal Monitoring Systems with Optical Disk Storage, New Technology Brief, (Nov./Dec. 1998), vol. 2, No. 6, pp. 249-251.
Cheng, Joe H., "PCT Search Report", (Jan. 11, 1996).
DigiPet Instruction Manual, 1997.
Digital Doggie; retrieved from URL http://www.virtualpet.com/vp/farm/gigapet/ddoggie.htm Apr. 23, 2000.
Douglas, A.S., et al., "Hand-Held Glucose Monitor and Recorder", Proceedings of the Annual International Conference of the IEEE Engineering in Medicine and Biology Society, New Orleans, LA, (Nov. 1988), pp. 747-748.
Edelson; "Fashion Reevaluates Flickering Fortunes of TV Home Shopping"; WWD v170 n87; p. 1(3); Nov. 8, 1995; Dialog: File 148, Acc#08289119.
EP European Search Report, From 6858P005EP, (Mar. 27, 1998).
O'Donnell; "Alan's At It Again"; Bond Buyer; v309 n29448; p. 1(3); Jul. 21, 1994; Dialog: File 148, Acc#07478152.
Onsale Joins Fray as Online Shopping Picks Up Speed: Internet Booms; Computer Reseller News; Jun. 5, 1995; p. 73; Dialog: File 16, Acc#05649796.
Onsale Onsale Brings Thrill of Auctions and Bargain Hunting Online; Unique Internet retail service debuts with week-long charity auction for the Computer Museum in Boston, May 24, 1995; Dialog Abstract: File 610, Acc#0489267.
Pfeiffer, E. F., "The Glucose Sensor: The Missing Link in Diabetes Therapy", Hormone and Metabolic Research, (1990), vol. 24m Suppl. pp. 154-164.
Playmates Toys deals knockout blow to virtual pet competitors with introduction of Nano Fighter™ for Boys; New Nano Pet Fighting Pet Press Release; retrieved from URL http://www.virtualpet.com/vp/farm/nano/nfightpr.htm Apr. 23, 2000.
Playmates Toys leads Americas virtual pet craze into its next generation by introducting talking Nano Pals; Talking Nano Pet Press Release; Nov. 18, 1997; retrieved from URL http://www.virtualpet.com/vp/farm/nano/talkn/tnpress.htm on Apr. 23, 2000.
Poitout, V., et al. "A Glucose Monitoring System for on Line Estimation in Man of Blood Glucose Concentration Using a Miniaturized Glucose Sensor Implanted in the Subcutaneous Tissue and a Wearable Control Unit", Diabetologia, (1993), vol. 36, pp. 658-663.
Polson, Gary "Recent Developments and Trends in Keychain Virtual Pets," 1997 [retrieved on Apr. 23, 2000], Retrieved from <URL:www.virtualpet.com/vp/future/trends1a.htm>.
Potter, David, "Fundamentals of PC-Based Data Acquisition", Sensors, (Feb. 1994), pp. 12-20.
Reis, H, "Telemedicine: Transmitting Expertise to the Point of Care Toward an Electronic Patient Record"; '97, Nashville, TN, Apr. 27-May 3, 1997, pp. 248-256, v. 3.
Research project launched to improve health of America's communities; new Disney community in Florida is focus of program. Business Wire, p. 10011142. Oct. 1, 1996.
Results of the world's first on-line auction, http://www.christies.com. RO_Auction Auctioneers Property Database System and RO_Auction Auctioneers Accounting System; RO-Auction features; Dec. 4, 1995.
Roberts; "Diabetes and Stress: A Type A Connection?", Psychology Today, (Jul. 1987), v. 21; pp. 22(1); Dialog: File 149, Acc# 05038381.
Rose, V. L., et al., "Decentralized Testing for Prothrombin Time and Activated Partial Thromboplastin Time Using a Dry Chemistry Portable Analyser", Archives of Pathology and Laboratory Medicine, (Jun. 1993), vol. 117, pp. 611-617.
Save the earth artrock auction, http://www.commerce.com.save-earth. Auction Web, http://www.ebay.com.
Schement, "An Intelligent Controller for Neurophysiological Experiments," Proceeding of the Annual Symposium on Computer Based Medical Systems, Durham, Jun. 14-17, 1992, p. 528, line 1-p. 529, line 21.
Schenkels, P., "Supplementary European Search Report", Application No. EP 97 92 2716, (Mar. 11, 2002).
Schork, Nicholas J., "Genetics of Complex Disease", Am.J.Respir. Crit. Care Me., (1997), vol. 156, pp. S103-S109.
Schrezenmeir, J. et al., "Computer Assisted Insulin Dosage Adjustment—Perspective for Diabetes Control", Hormone and Metabolic Research, Supplement Series, (1990), vol. 24, pp. 116-123.
Seigmann;"Nowhere to Go but Up"; PC Week; v12 n42, p. A5(1); Oct. 23, 1995; Dialog: File 148, Acc#08222496.
Seybold—New Horizons teams with Duke, Real Media; the Seybold Report on Desktop Publishing, v10 n12 p. 24(1), Aug. 12, 1996.
Shandle, Jack, "Who Will Dominate the Desktop in the 90's?", Electronics, Feb. 1990, pp. 48-50. (3 pages).
Shults, Marc C., et al., "A Telemetry-Instrumentation System for Monitoring Multiple Subcutaneously Implanted Glucose Sensors", IEEE Transactions on Biomedical Engineering, (Oct. 1994), vol. 41, No. 10, pp. 937-942.
Skolnick et al. "Simultaneous Analysis of Multiple Polymorphic Loci Using Amplified Sequence Polymorphisms (ASPs)"; Genomics. 2: 273-279.
Soeldner, J. S., "Treatment of Diabetes Mellitus by Devices", The American Journal of Medicine, (Jan. 1981), vol. 70, 183-194.
Spitzer et al.; "The moderating effect of age on self-care"; Western Journal of Nursing Research, v18, n2, p. 136(13), Apr. 1996.
Symbol Technologies; "Healthcare Mobility Solutions for the PPT8800", Feb. 2004.
Talking Nano Puppy; retrieved from URL http://www.virtualpet.com/vp/farm/nano/talkn/talkn.htm Apr. 23, 2000.
Tamagotchi, 1997 [retrieved on Apr. 23, 2000], Retrieved from <URL:www.virtualpet.com/vp/farm/lleg/lleg.htm>.
Tandy Radio Shack , "The description of the Tandy Radio Shack TRS-80 Model 100/102 device available at http://www.old-computuers.com/musuem/computer.asp?c=233", World Wide Web, (Feb. 13, 2004), 1-3.
Telemedicine Provides Two-Way Computer Link for Parents of Very Premature Infants. PR Newswire. p1007NEM034. Oct. 7, 1996.
Theme Hospital, product review 1996 [retrieved Apr. 21, 2000], Retrieved from <URL:www.vigilante.co.uk/ep/misc/hospital.htm>.
Towards a partnership of care, M2 Presswire, Jun. 14, 2000.
United Healthcare's OPTUM Division goes online to better health by announcing a unique internet application. PR Newswire, p0801MNTH004. Aug. 1, 1996.
Updike, Stuart J., et al., "Laboratory Evaluation of New Reusable Blood Glucose Sensor", Diabetes Care, (Nov./Dec. 1998), vol. 11, No. 10, pp. 801-807.
Valla, et al., "A Structured Pictorial Questionnaire to Assess DSM-III-R-based Diagnosis in Children (6-11 years)"; Journal of Abnormal Child Psychology; v22 n4; p. 403(21); Aug. 1994; Dialog: File 88, Acc# 15759542.
Vallera, D. A., et al., "Accuracy of Portable Blood Glucose Monitoring", American Journal of Clinical Pathology, (1991), vol. 95, No. 2, pp. 247-252.
Virtual Pet Product Reviews, 1997 [retrieved on Apr. 23, 2000], Retrieved from <URL:www.virtualpet.com/vp/farm/reviews/reviews,htm>.
Virtual Tomagutchi, 1998 [retrieved Apr. 23, 2000], Retrieved from <URL:www.sttf.org/english/action/tomagutchi.html>.

(56) References Cited

OTHER PUBLICATIONS

Voelker, Rebecca, "Shoe Leather Therapy is Gaining on TB", Jama, (Mar. 13, 1996), vol. 275, 743.
Wilkins, Aaron. "Expanding Internet access for health care consumers", Health Care Management Review, Summer, Jul. 1999, 24-30.
Wyatt, J. C., "Clinical Data Systems, Part 2: Components and Techniques", Lancet, (Dec. 1994), vol. 344, No. 8937, pp. 1609-1614.
Yoshizawa, Daisuke, et al., "The Development of a Data Processing System with Personal Computer MSX Standard System for Flow Injection Analysis", Journal of Flow Injection Analysis, (1988), V.5, No. 2, pp. 101-110.
Fabietti, P.G., et al., "Wearable System for Acquisition, Processing and Storage of the Signal from Amperometric Glucose Sensors", The International Journal of Artificial Organs, (1991), vol. 14, No. 3, pp. 175-178.
Finston, "Parent + Teacher = Healthy Child", Diabetes Forecast, (Apr. 1994), v47 n9; p. 26(5); Dialog: file 149, Acc# 15804228.
Fox, "Not My Type: Type B Behavior, Type I Diabetes Plus Stress Equals Blood Sugar Blues", Health, (Mar. 1998), v20 n3; pp. 22(1); Dialog: File 149, Acc# 06397959.
Franklin; "Proposed Auction Rules for PCS: The FCC Plans to Use Competitive Bidding, but Exact Procedures are Undefined"; Cellular Business; v10 n13; p. 18(2); Dec. 1993; Dialog: File 148, Acc#06787310.
Frieberger, Paul, "Video Game Takes on Diabetes Superhero 'Captain Novolin' Offers Treatment Tips", San Francisco Examiner, (Jun. 26, 1992), Fourth Edition, Business Section B1.
Furnham, et al; "Measuring Locus of Control: a Critique of General Children's Health- and Work-related Locus of Control Questionnaires"; British Journal of Psychology; v84 n4; p. 443(37); Nov. 1993; Dialog: File 88, Acc# 14903135.
Future of the Virtual Pet Industry, 1997 [retrieved on Apr. 23, 2000], Retrieved from <URL:www.virtualpet.com/vp/future/future.htm>.
Gardner, et al.; "Comprehension and Appreciation of Humorous Material Following Brain Damage"; Brain; Sep. 1975; 98(3); pp. 399-412; Dialog: File 153, Acc#02859983. (14 pages).
Gauntlet (for PC) rulebook by Mindscape Inc. (Gauntlet by Apple);1985.
Giga Farm; retrieved from URL http://www.virtualpet.com/vp/farm/gigapet/gpfarm.htm Apr. 23, 2000.
Giga Pets, 1997 [retrieved on Apr. 23, 2000], Retrieved from <URL:www.virtualpet.com/vp/farm/gigapet/gigapet.htm>.
Gordon; "Auctions Become High Tech"; Dealer Business; v29 n7; p. 21(4); Mar. 1995; Dialog: File 148, Acc#07862519.
Guiffrida, et al., Should We Pay the Patient? Review of Financial Incentives to enhance Patient Compliance:, Biomedical Journal, (1997), vol. 315, pp. 703-707.
Hauben, Jay R., "A Brief History of the Cleveland Free-Net", available at http://www.ais.org/~irh/acn7-1.a09.html, (1995) pp. 1-4.
Hauser, et al., "Will Computers Replace or Complement the Diabetes Educator?", The Medical Journal of Australia, (Oct. 5, 1992), vol. 157, 489-491.
Horio, Hiroyuki, et al., "Clinical Telecommunication Network System for Home Monitoring", Medical & Biological Engineering & Computing, (Mar. 1994), vol. 32, 227-230.
How Flash Memory Works, Internet printout of URL address: http://www.howstuffworks.com/flash-memory4.htm, (Sep. 28, 2002), 2 pages.
Howey, et al., "A Rapidly Absorbed Analogue of Human Insulin"; Diabetes, vol. 43, Mar. 1994, pp. 396-402. (7 pages).
Hunter, "Technological Advances in Bedside Monitoring: Biosensors", Archives and Laboratory Medicine, (Jul. 1987), pp. 633-636.
Hutheesing, Nikhil, "An on-line gamble", Forbes, v157 n10 p. 288(1), May 20, 1996.
Introducing the Next Generation of About Your Diabetes, U.S. Pharmacopical Convention and American Diabetes Association, (1993).
Jaffrey et al.; "PIN: An Associated Protein Inhibitor of Neuronal Nitric Oxide Synthase"; Science; vol. 274; Nov. 1, 1996; Ref: XP 002050141.
Jimison et al., "Patient-Specific explanation in models of chronic disease", Revised Feb. 1992 Artificial Intelligence in Medicine 4 (1992) 191-205.
Jones, Chris, "Microsoft readies DocObject; technology will allow document editing in Web browsers", InfoWorld, v18 n18 p. 48(1), Apr. 29, 1996.
Kauffmann, et al., "Epidemiological Study of the Genetics and Environment of Asthma Bronchial Hyperresponsiveness and Atrophy", Am. J. Respir. Crit. Care Med., (1997), vol. 156, pp. S123-S129.
Kaufman, Steven, B., "The Learning Game", Nation's Business, (Nov. 1993).
Kennedy et al.; "Television Computer Games: a New Look in Performance Testing"; Aviat Space Environ Med; Jan. 1982, 53(1); pp. 49-53. (5 pages); Dialog Abstract: File 155, Acc#0353751.
Kuykendall, V.G., et al., "Assessment of Self-Monitored Blood Glucose results Using a Reflectance Meter with Memory and Microcomputer", Symposium on Computer Applications in Medical Care, (Jan. 1981), vol. 70, pp. 98-102.
Lachnit, Carroll, "Hawkin's Online Auction", Photo District News, vol. 16, Issue 1, p. 18, Jan. 1996.
Lacyk, John, "PCT Search Report", (Jun. 12, 1997).
Latman, N.S., "Evaluation of Electronic, Digital Blood Glucose Monitors", Biomedical Instrumentation and Technology, (1991), vol. 25, No. 1, 43-49.
Leyerle, Beverly J., et al., "The PDMS as a Focal Point for Distributed Patient Data", International Journal of Clinical Monitoring and Computing, (1988), vol. 5, pp. 155-161.
Luebke, Cathy, "Barrett-Jackson Auction Turns High-Tech", Business Journal, vol. 16, Issue 12, pp. 11, Jan. 19, 1996.
Makikawa, M., et al., "Microprocessor-Based Memory Device for Ambulatory Heart Rate and Physical Activity Recording", Methods of Information in Medicine, (1994), vol. 33, No. 1, pp. 94-96.
Marsh, David G. "Approaches Toward the Genetic Analysis of Complex Traits Asthma and Atrophy", Am. J. Respir.Crit.Care Med., (1997), vol. 156, pp. S-133-S138.
Martinez, Fernando D., "Complexities of the Genetics of Asthma", Am.J. Respir. Crit. Care Med., (1997), vol. 156, pp. S117-S122.
Marx, Wendy, "More than just the Scores: ESPNET SportsZone is a model for expanding brand names online", InformationWeek, n576 p. 61(2), Apr. 22, 1996.
Mazzola, et al., "Video Diabetes: A Teaching Tool for Children with Insulin-Dependent Diabetes", Proceedings—7th Annual Symposium on Computer Applications in Medical Care; Washington, DC; Dialog:, (Oct. 1983), File 8, Acc# 01624462.
McCullagh, PJ et al., "Computerized paradigms for eliciting the contingent negative variation event-related potential," Proceedings of the Annual International Conference of the Engineering in Medicine & Biology Society, IEEE, Conf. 14, p. 2481-2483, Oct. 1992.
Meissner, et al., "Building an Integrated Clinical and Research Network", Proceedings of the SPIE, (Oct. 24, 1995), vol. 2618, p. 92-99.
Miles, Laughton E., "A Portable Microcomputer for Long-Term Physiological Monitoring in the Home and Work Environment", Medical Monitoring in the Home and Work Environment, (1990), pp. 47-57.
Mims; "Psychological Testing"; Computers & Electronics; v23; p. 22(6); Feb. 1985; Dialog: File 47, Acc# 2654858.
Moore, "New Applications Break Through Storage Boundaries", Computer Technology Review, (Oct. 1999), vol. 19, No. 10 p. 1.
Mule. rulebook by Electronic Arts, 1983.
Nano Baby Instructions; retrieved from file://C:\My Documents \Nano Baby Instructions.htm Apr. 23, 2000.
Nano Fighter Pets; retrieved from URL http://www.virtualpet.com/vp/farm/nano/nfighter.htm Apr. 23, 2000.
Nano Page, 1997 [retrieved on Apr. 23, 2000], Retrieved from <URL:www.virtualpet.com/vp/farm/nano/nano.htm>.
Octhigotchi Instruction Manual, 1997. Dino-Kun Instruction Manual, 1997.

* cited by examiner

| Threat Status | Low Threat | Suspicion or high risk event | Confirmed threat, outbreak or attack |
|---|---|---|---|
| Description | Passive Surveillance and continuous education | Active surveillance with anonymous data | Quarantine and patient identified data |
| Pharmacy | Passively collect data from over-the-counter sales | Interact with pharmacist | Pharmacist interviews patients |
| Hospital | Passively collect chief complaint data, tally sheets of syndrome data, continuous daily education | Actively survey for additional data each patient entering ED. Anonymous data. | Patient identified data and reporting. |
| Home | Citizens sentinel network of volunteers report syndrome data | Additional active monitoring of vulnerable populations in existing monitoring programs | Initiate monitoring of any high risk or exposed individual, patient identified data |

FIG. 6

Does the patient have ... (choose the first that applies)
1. Fever
2. Acute GE (N or V and D)
3. Acute Weakness/Facial Paralysis
4. None of the above
| 1 | 2 | 3 | 4 |
Does the patient have ... (choose the first that applies)
1. A rash
2. Altered mental status
3. Cough/shortness of breath
4. None of the above
| 1 | 2 | 3 | 4 |
Has this patient attended a large public group gathering in the past 2 weeks?
| Yes | No |
FIG. 10

| Requirement | Current Process | Health Hero Network Advantage |
|---|---|---|
| Ease of data entry and reporting | o Manual, faxed | o Push-button data capture<br>o Automatic transmittal to central system |
| Conditional questions | o One level of inquiry | Does patient have a fever?<br>NO → Does patient have diarrhea?<br>YES → Does patient have a rash? |
| Dynamically adapts to new information requirements | o Static questions | *9:23 a.m. – Follow-up Question:*<br>Has patient been in a large group gathering?<br>*9:58 a.m. – Follow-up Question:*<br>Has patient handled suspicious mail? |

FIG. 12

|  | Luna, Craig | HEALTH HERO |
|---|---|---|
| Find Patient [  ] GO | Fri, April 4, 2003 | NETWORK |
| (Last Name) | ▷ Contact Health Hero  ▷ Help  ▷ Log Out | |

| Home | Patient | Reports | Enrollment | Disenrollment | Schedule | Setup |
|---|---|---|---|---|---|---|
| Work List | Profile | Results | Trends | Notes | | |

Use these options to change the work list below.

1. Show patients from which program?   2. For which session date?   3. For which care management?

[ ------ All Programs ------ ▽ ]   [ 11/19/2003 ▽ ]   [ ---- All Care Managers ---- ▽ ]

Printer friendly version                              [Create Work List]

---

| You are viewing sessions for Nov 19, 2003 in the "All Programs" Program | Date: ◁ ▷ |
|---|---|

| Responders' Risk Summary |  |  |  |  |
|---|---|---|---|---|
|  | Symptoms | Behavior | Knowledge | General |
| High Risk | 2 | 2 | 0 | 0 |
| Medium Risk | 0 | 1 | 2 | 0 |
| Low Risk | 6 | 5 | 4 | 2 |
| None | 0 | 0 | 0 | 6 |

| Patient Summary | |
|---|---|
| Responders | 8 |
| Non-Responders | 4 |

| Responses on Monday, November 19, 2003 | | | | | |
|---|---|---|---|---|---|
| Patient | Response Time | Sympt. | Bhvr. | Kwldg. | Gen. |
| Lang, Nancy | 08:38 AM PST | High | High |  | Low |
| Cherry, Julie C. | 08:41 AM PST | High | Low | Low | None |
| Beninger, Jennifer | 11:15 AM PST | Low | High | Medium | None |
| Messing, Mel | 10:16 PM PST | Low | Medium |  | None |
| Lapp, Mary | 09:38 AM PST | Low | Low | Medium | None |
| Coll, Laurie | 10:09 PM PST | Low | Low | Low | None |
| Hoff, Jane | 11:14 AM PST | Low | Low | Low | Low |
| Man, Marie | 09:12 AM PST | Low | Low | Low | None |

Back to Top

FIG. 16 (a)

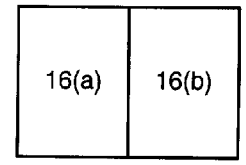

FIG. 16

Demo Library / Demonstration day dialogues
Health Hero NETWORK

Demo Library / Demonstration day dialogues
Diabetes Day
Health Hero NETWORK

Demo Library / Demonstration day dialogues
COPD Day
Health Hero NETWORK

Demo Library / Demonstration day dialogues
CHF Day, 0101
Health Hero NETWORK

Legend" 0=No Risk  @=Low Risk  &=Medium Risk  #=High Risk

?Welcome back, Pat! Thank you for using the Health Buddy. Begin whenever you are ready
[Greeting 2: None / General]
?Did you weigh yourself today? [Did you weigh today?: Weight / Behavior]
   @Yes
      ?What is your weigh today? (Use the arrows to indicate your weight)[Weighttrend: Weight / Symptoms]
         ?(Q[Weight trend]>(M[High Weight]+2))
            0 True
               ?This is much higher than your usual weight. Sometimes weight can be affected by heavy clothing or shoes. Please be sure that you weighed yourself without heavy clothing or shoes. [Much higher: Weight / Symptoms]
                  #Okay
                     ?Remember, if your weight is up 3 or more pounds, call Dr. Welby today at 555-1212. [Reminder: Weight/ Symptoms]
            0 False
               ?(Q[Weight trend] = (M[High Weight]+2))
                  0 True
                     This is somewhat higher than your usual weight. Sometimes weight can be affected by heavy clothing and shoes. Please be sure that you weighed yourself without heavy clothing or shoes. {Somewhat higher: Weight / Symptoms]
                        &Okay
                     (Q[Weight trend]=(M[High Weight]+1))
                        0 True
                           ?This is slightly higher than your usual weight. Sometimes weight can be affected by heavy clothing and shoes. Please be sure that you weighed yourself without heavy clothing or shoes. [Slightly higher: Weight / Symptoms]
                              @Okay

FIG. 17

REMOTE HEALTH MONITORING SYSTEM

CLAIM OF PRIORITY

This is a continuation of U.S. Ser. No. 10/840,945, filed May 7, 2004 now U.S. Pat. No. 7,399,276, which claims the priority of U.S. Provisional Application No. 60/469,453 filed May 8, 2003, each of which is incorporated herein by reference.

FIELD OF THE INVENTION

This invention relates generally to remote health monitoring systems, as applied to the field of public health surveillance. In particular, it relates to a multi-user remote health monitoring system that is capable of reliably identifying and collecting data from frontline healthcare providers, laboratory and hospital information systems, patients and healthy individuals in a number of ways, with a view to aid in the field of public health. The system can also be used to query and collect additional information regarding specifics pertaining to the health of the individuals, and for patient tracking, monitoring, and the collection of individual data.

BACKGROUND OF THE INVENTION

Recent events including the ongoing Severe Acute Respiratory Syndrome (SARS) Epidemic underscore the constant public health threat faced by the United States with regard to new and emerging infectious diseases.

There is a need for a disease surveillance system that reduces time-to-detection monitors preparedness at the local level, and automatically integrates information from range of sources and facilitating investigations and enabling rapid statistical analyses to performed. The surveillance systems should monitor the health of the population in real and on a continuous basis. Many disease agents offer only a brief window between exposure and the onset of symptoms. In addition, many agents, like anthrax, cannot be successfully treated once the condition has become advanced but can be treated if caught early. Thus, window of time during which effective intervention is possible can be very narrow. In to facilitate rapid responses, surveillance systems must be capable of monitoring information on an ongoing basis. In order to intervene successfully to treat existing infections and prevent the onset of new ones, health surveillance systems should provide a continuous, realtime (or as near real-time as possible), and accurate overview of a population's health. Monitoring, and following up individuals who present themselves at healthcare facilities in both the emergency and the routine setting, and monitoring the results of laboratory and radiological investigations, routine hospital census information and autopsy reports of unexplained deaths would help accomplish this in real life.

Information systems that integrate data collected over multiple healthcare facilities and large populations enable dedicated public health analyst(s) at the Health Departments to attach significance to seemingly disparate events, and subsequently recognize the occurrence of a biological event far earlier than if it were done on an individual basis at an individual healthcare facility.

Current infectious disease reporting systems typically wait until the diagnosis of a specific disease before the care provider reports to the public health department. Crucial time is also lost from when a test is reported as positive to its report reaching the physician who ordered it. Many possible bioterrorism agents do not present with specific symptoms in the early stages of the disease and therefore are difficult to identify. This means that care providers have to wait until the disease has progressed to advanced stages before they report to the local health department. Given the contagious nature of many targeted diseases and the potential threat of cross contamination from biological agents, the early identification of biological attacks is imperative. The ability to quarantine or decontaminate exposed populations thereby preventing further dissemination of harmful agents will be greatly facilitated by the use of active surveillance and monitoring.

Last year, there were approximately 100 million emergency room visits in the United States. Therefore, each of the approximately 4,200 emergency rooms received on average of 66 visits per day, with some larger emergency departments at academic medical centers and major trauma centers experiencing greater than 150 visits per day. If the scope of surveillance is expanded to include physicians' offices, walk-in clinics, laboratory and radiological data, and hospital information systems the requirements for the successful collection of information on each patient's symptoms, become particularly challenging.

Many emergency care facilities currently participate in rudimentary active surveillance programs. Such programs typically involve paper-based surveys that are faxed to a central county location for manual tabulation. In addition to their time consuming nature, paper-based surveys greatly reduce the ability to query discrete data elements, limit the ability to change the data elements collected in response to a new event, and are much more open to errors due to manual recording, tabulation and data entry.

For an active surveillance system to succeed, it must have the following characteristics: real time data collection, low burden of data entry and maintenance on healthcare providers, ability to dynamically respond to new information, ability to collect data from a wide range of settings (ERs, clinics, physicians' offices, laboratories, hospital information systems etc.), ability to aggregate data across jurisdictions and regions, ability to collect incrementally more information about high-risk patients, two way communication capabilities to provide immediate feedback and education to frontline healthcare providers. The invention described below enables public health officials do this in an inexpensive and convenient manner. In addition, the system may be used to automate components of standard hospital procedures/protocols, and save precious time to detection in case of the unfortunate occurrence of such an event.

BRIEF DESCRIPTION OF THE DRAWINGS

FIG. 6 is a table of a BASIICS model.

FIG. 10 is diagram showing an example set of screens on a Health Buddy.

FIG. 12 is a table comparing the Health Hero network with a conventional process.

FIG. 16(a) depicts details of the example patient profile of FIG. 16.

FIG. 16(b) depicts details of the patient summaries of FIG. 16.

FIG. 17 is a diagram of example interactive dialogues.

DETAILED DESCRIPTION OF THE DRAWINGS

Figure 1:
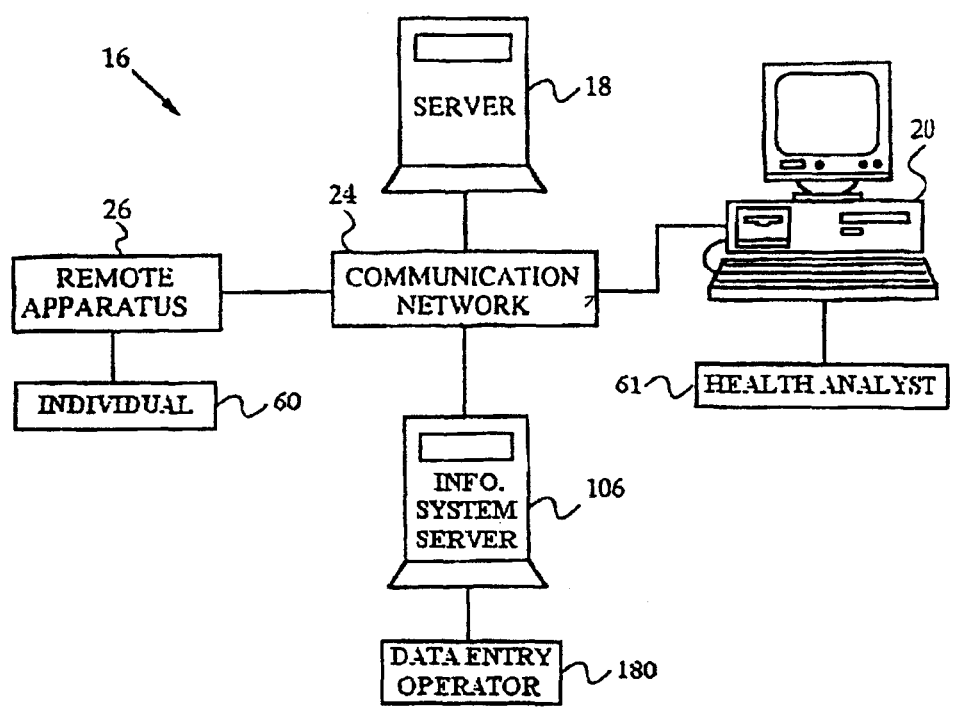
FIG. 1 is a block diagram of a networked system according to a preferred embodiment of the invention.

Referring to FIG. 1, a networked system 16 includes a server 18, a workstation 20, an information system server 106 connected to a remote apparatus 26 through a communication network 24. Communication network 24 is any network that allows the transmission of data between server 18, workstation 20, remote apparatus 26 and information system server 106.

Network 24 may suitably include a wireless communication network, cellular network, telephone network, local area network (LAN), wide area network (WAN), storage area network (SAN), Wireless in Local Loop (WLL) network, virtual private network WPN), WiFi network, digital television network, or the Internet. The server 18 is preferably a server that is capable of communicating data on more than one such communication network 24. It will be apparent to one of ordinary skill in the art that the server 18 may comprise a single stand-alone computer or multiple computers distributed throughout a network.

An individual 60 uses the apparatus 26 to communicate with the system 16. Individual 60 may be any person whose health status is being monitored by the system 16. For one non-limiting example, the individual 60 is a person who has been exposed to a disease causing agent, or another individual who has developed a specified disease. For another example, the individual 60 is a person who is enrolled in a community "sentinel surveillance" program, whereby the health of a certain percentage of individuals in the community is constantly monitored for the development of disease.

Additionally, the individual 60 may be a person who is on a remote health management program for a chronic disease, and whose health is being additionally monitored as a part of "sentinel surveillance". For one non-limiting example, the system 16 additionally monitors the health of patients in a COPD (Chronic Obstructive Pulmonary Disease) disease management program. An advantage of monitoring patients with chronic diseases, and incorporating this data into a public health surveillance system is that such patients are inherently more vulnerable to the development of disease, and are likely to exhibiting disease manifestations at an earlier point in time. The monitoring improves the sensitivity of the system, and reduces the time-to-detection of an outbreak. An advantage to the patient is a more intensive monitoring, and an overall better health outcome. It will be apparent to one of ordinary skill in the art that patients with any chronic disease, (e.g., elders with Congestive Heart Failure, children with Asthma or Type I Diabetes) may be monitored for the purpose of public health surveillance. An advantage to the patient is an increased level of monitoring and a more responsive disease management, which ultimately leads to a better health outcome.

Further, the individual 60 may be a caregiver at a healthcare facility, suitably including a Triage Nurse at an Emergency Department. The triage nurse inputs information on a plurality of patients reporting at a healthcare facility. Additionally, patient information and measurements are taken by the remote apparatus for input into the system 16.

Apparatus 26 is any device that allows the communication between the individual 60 and the system. In a preferred embodiment of the invention, the apparatus 26 is a consumer communication device that suitably includes a data receipt means, a display unit, a data input means, a data transmission means, a physiological variable measuring means, a patient identification means, a data-storage means, a system logic means and a geographical localization means.

In a preferred embodiment of the invention, the apparatus 26 is capable of making a measurement 44 (not shown) of at least one physiological variable of an individual. The physiological variable may be any measurement that helps in the detection of disease or disease related changes in an individual suitably including body temperature, pulse rate, respiratory rate and skin galvanic conduction. Additionally the physiological variable may include any measurement that will enable the positive identification of the individual, suitably including a digital fingerprint, a retinal scan, or a DNA assay. The apparatus 26 is designed to interact with a plurality of individuals in accordance with script programs received from the server 18. The apparatus 26 is in communication with the server 18 through the communication network 24, preferably a wireless communication network.

Alternatively, the remote apparatus 26 may be any electronic device that is capable of displaying queries and transmitting the responses of the individual 60 to the server 18. For one non-limiting example, the remote apparatus 26 is a remote communication enabled Personal Digital Assistant (PDA) and the individual 60 replies to queries received from the server 18. Alternatively the remote apparatus 26 is a personal computer connected to the internet and the individual replies to queries that are displayed on a webpage. Alternatively the apparatus 26 is an interactive television set and the responses of the individual 60 to queries are transmitted through a digital television network to the server 18. It is apparent that many other electronic devices and communication systems may be used to this end.

A health analyst 61 uses the workstation 20 to analyze the data that is made available from within the system 16. The analyst 61 is any person with the requisite expertise, and who is authorized to access the system 16. Workstation 20 is preferably a personal computer connected to the server 18 via a secure internet connection. The workstation 20 serves as an interface for health analyst 61 to analyze the health monitoring data of the individual 60 that is made available through remote apparatus 26 and information system server 106. In addition, the analyst uses workstation 20 to enter messages, queries and requests for physiological measurements of the monitored individual 60.

Information system server 106 may be any computer system that contains health related information of the individual 60. Information system server 106 suitably includes hospital information systems, diagnostic laboratory and radiological information systems, hospital administrative and billing information systems and pharmacy inventory and billing systems. Additionally, Information system server 106 includes such sources of information that provide the general health information of groups of individuals. At each Information system server 106, a Data Entry Operator 180 inputs health and related data.

For one non limiting example, system server 106 is located in a pharmacy, and the operator 180 is a pharmacist who inputs data relating to the sales of specified medication, such as over the counter (OTC) medication e.g. a cough syrup. The information is inputted into the system 16 and an abnormal increase in the sales of the specified medication is used as a possible indicator of a developing epidemic. Analyst 61 may review the data, and additionally may communicate with the pharmacist to elicit specific data relating to the epidemic.

For another non-limiting example, system server 106 is located in the emergency medical department of a hospital, and operator 180 is a caregiver who inputs patient data into the information system. For another non-limiting example, system server 106 is located in a school, and the information inputs is the attendance and information on the children who have reported sick on a particular day.

For clarity of illustration, only one apparatus 26 and information system server 106 is shown in FIG. 1. It is to be understood that the system 16 may include any number of apparatuses, and servers with each apparatus and server used to retrieve health related information about any number of individuals.

Figure 2:
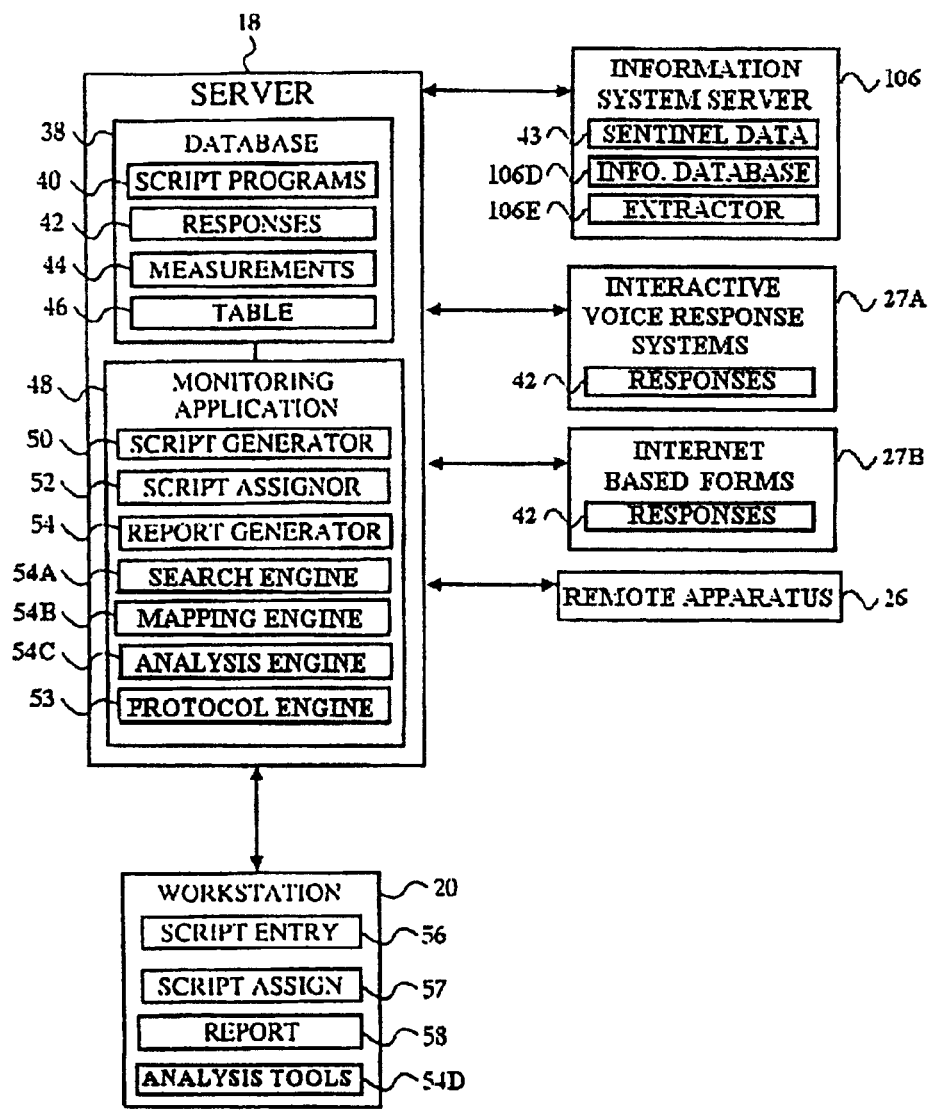
FIG. 2 is a block diagram illustrating the interaction of the components of the system of FIG. 1.

FIG. 2 shows the server 18, the workstation 20 and the information system server 106 in detail. Information system server 106 includes an information database 106D, an extractor program 106E and a sentinel data 43. Information database 106D suitably includes the data within the information system server 106 that is of public health significance. For one non-limiting example, in a pharmacy server, database 106D includes data on the number of units of a specified medication that were sold in a given period of time. In a healthcare facility, information database 106D includes the information on the number of patients who presented with a particular set of symptoms, or tested positive for a particular disease agent. Extractor program 106E is a computer program that is installed on the server 106. Extractor program scans the data in information database 106D to extract sentinel data 43, which contains the information in a standardized format, for transmission to server 18.

The server 18 includes a database 38 for storing script programs 40. The script programs 40 are executed by the apparatus 26 to communicate queries and messages to the individual 60, receive responses 42 to the queries, collect physiological measurements 44, and transmit the responses 42 and the measurements 44 to the server 18. The database 38 is designed to store responses 42 and measurements 44. The database 38 further includes a look-up table 46. The table 46 contains a list of individuals, healthcare facilities, and data sources within the healthcare facilities that provide data inputs into the surveillance system; and for each entity, a unique identification means and a pointer to the script program 40. Each apparatus 26 is designed to execute assigned script programs 40 which it receives from the server 18.

The server 18 further includes a monitoring application 48. The monitoring application 48 is a controlling software application executed by the server 18 to perform its various described functions. The application 48 includes a script generator 50, a script assignor 52, a report generator 54, a search engine 54A, a mapping engine 54B, an analysis engine 54C and a protocol engine 53.

The system 16 further includes an interactive voice response system 27A (IVRS 27A) a telephone based reporting system, and an inter-net based form 27B (IBF 27B) that allow for the reporting of unstructured information into the system 16 by caregivers, who notice a rare or unusual occurrence that is suspicious and/or indicative of an impending outbreak; in order to bring this information to the attention of analyst 61. It is also used advantageously by caregivers and citizens who are otherwise not covered by the system 16 to report disease data, and as a source of information.

Responses 42 of Database 38 archive data of the individual 60 from information sources. The data is further processed by the search engine 54A, mapping engine 54B and analysis engine 54C to highlight to the analyst 61 the information that is suspicious of a disease outbreak. The analyst 61 may use the analysis tools 54D to further analyze the information within responses 42. The analysis tools 54D interfaces with search engine 54A, mapping engine 54B, and analysis engine 54C using application program interfaces (API) to generate a report 58 for display on workstation 20.

Search Engine 54A works like an internet search engine and scans responses 42 for data that may indicate an outbreak. Mapping engine 54B creates graphical visualizations of responses 42 and sentinel data 43 permitting analysis by analyst 61. Further, mapping engine 54B uses visual interpretative and graphical processing methods to analyze the images for abnormal data. Analysis engine 54C automatically analyzes the responses 42 and sentinel data 43, to bring to the attention of analyst 61 abnormal or other data that is likely to signify an impending outbreak. Protocol Engine 53 is an API that permits the monitoring application 48 to automatically assign the script program 40 on the basis of the latest information in responses 42.

In case the analyst 61 determines that more information is needed in a certain case, he/she uses a script entry screen 56 and a script assign screen 57 to create and assign script program 40 to the individual 60, which may be an individual citizen or a caregiver at a healthcare facility.

Specific techniques for generating scripts for transmission to remote devices, for assigning scripts to specified individuals, for creating the script generator 50, the script assignor 52, the report generator 54, the search engine 54A, the mapping engine 54B, the analysis engine 54C, the protocol engine 53 are given in U.S. patent application Ser. No. 10/279,749; filed Oct. 23, 2002; inventors Brown, et al., herein incorporated by reference.

Figure 3:
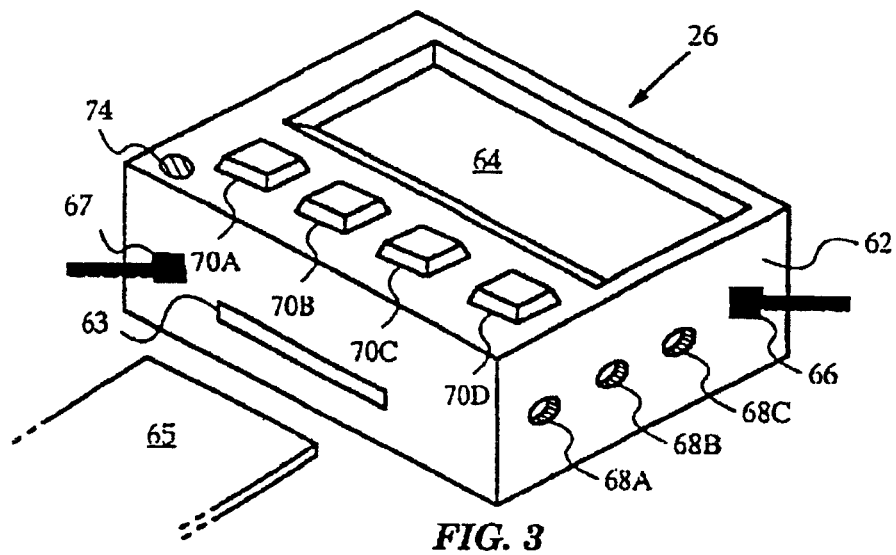
FIG. 3 is a perspective view of a remotely programmable apparatus of the system of FIG. 1.
Figure 4:
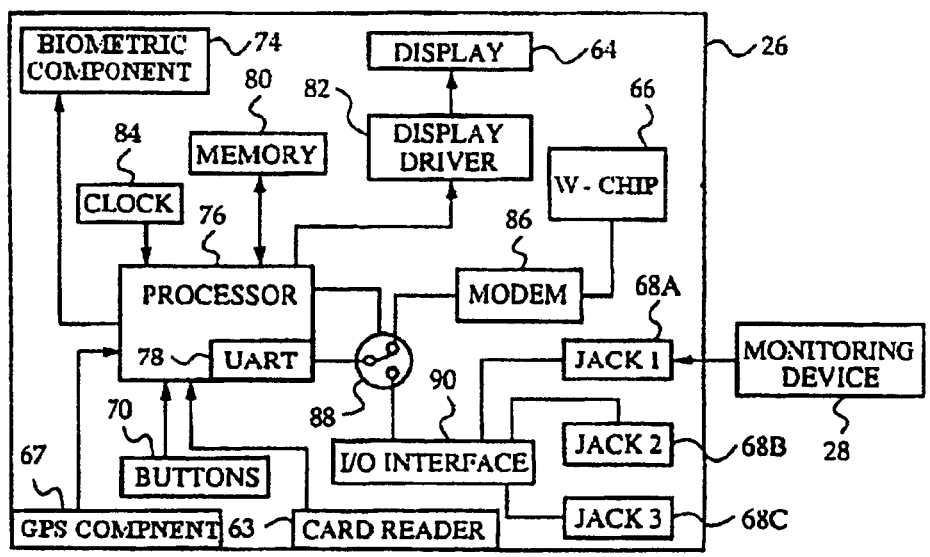
FIG. 4 is a block diagram illustrating the components of the apparatus of FIG. 3.

FIGS. 3-4 show the structure of each apparatus 26 according to the preferred embodiment. Referring to FIG. 3, the apparatus 26 includes a housing 62. The housing 62 is sufficiently compact to facilitate the easy handling of the apparatus, and for it to be kept on the person of the individual 60. The apparatus 26 also includes a display 64 for displaying queries and prompts to the individual. In the preferred embodiment, the display 64 is a liquid crystal display (LCD).

Four user input buttons 70A, 70B, 70C, and 70D are located adjacent to the display 64. User input buttons 70A, 70B, 70C, and 70D are for entering in the apparatus 26 responses to the queries and prompts. In the preferred embodiment, user input buttons 70A, 70B, 70C, and 70D are momentary contact push buttons. In alternative embodiments, the user input buttons 70A, 70B, 70C, and 70D may be replaced by switches, keys, a touch sensitive display screen, or any other data input device.

Three monitoring device jacks 68A, 68B, and 68C are located on a surface of housing 62. Device jacks 68A, 68B, and 68C are for connecting the apparatus 26 to a monitoring device 28. Monitoring device 28 is an attachment to the apparatus which enables the measurement of a physiological variable. For one non-limiting example, device 28 is a digital thermometer that measures the body temperature of the individual 60. Device 28 may be a digital pulse oximeter that measures the pulse rate and oxygen saturation in the capillary blood of the individual 60. Additionally, monitoring device is a skin galvanic conduction meter that measures the electrical conduction across the skin of individual 60. Many other devices are available for the measurement of physiological variables in the individual.

In an alternate embodiment of the invention, device 28 is automated chemical and toxicological analyzers, radiological meter (e.g. Geiger counter) which is attached to the apparatus 26, through respective connection cables (not shown). An advantage of this embodiment is that the apparatus 26 may be placed in a care facility or as a part of a First Responder Unit for immediate assessment of the individual 60 and communication of this information to the system 16.

The apparatus 26 also includes a wireless-chip 66 for receiving and communicating data with the server 18. Wireless-chip may be any generic cellular phone/global phone chip with an embedded transmitter and receiver. The apparatus 26 further includes a biometric identifier component 74. Biometric identifier component 74 is any component, including a microprocessor embedded component that allows the device to identify the individual 60. For non-limiting examples, component 74 may be a fingerprint scanner, a voice identification device, an iris scanner, a retinal scanner, a DNA micro-array scanner, etc.

The apparatus 26 also contains a data card reader 63. The data card reader 63 is capable of reading a data card 65 containing information about the individual 60. In the present invention, the data card 65 contains the identity of the individual and/or the healthcare facility, and the respective authentication codes. The data card 65 is placed in the data card reader 63, thus allowing the apparatus 26 to store information of the individual locally, and assign the script program 40. The apparatus 26 also has an embedded global positioning system (GPS) component 67, allowing the system to elicit information on the geographical location of apparatus 26.

FIG. 4 is a schematic block diagram illustrating the components of the apparatus 26 in detail. The apparatus 26 includes a microprocessor 76, and a memory 80 connected to the microprocessor 76. The memory 80 is preferably a non-volatile memory, such as a serial EEPROM. The memory 80 stores script programs 40 received from the server 18, measurements 44 received from the monitoring device 28, responses to queries, and individual's unique identity from biometric identifier component 74, and/or data card reader 63. The microprocessor 76 also includes built-in read only memory (ROM, which stores firmware) for controlling the operation of the apparatus 26. The firmware includes a script interpreter used by the microprocessor 76 to execute script programs 40. The script interpreter interprets script commands, which are executed by the microprocessor 76.

The script commands allow apparatus 26 to identify the operator through user buttons 70A, 70B, 70C, and 70D, the biometric identifier component 74 or the data card 65. They also allow the apparatus 26 to display the query sets to the individual 60 receive responses 42 to the query sets, receive measurements 44 from the monitoring device 28, and transmit responses to the server 18. Specific techniques for interpreting and executing script commands in this manner are well known in the art.

The microprocessor 76 is preferably connected to the memory 80 using a standard two-wire 12C interface. The microprocessor 76 is also connected to user input buttons 70A, 70B, 70C, and 70D, data card reader 63, biometric identifier component 74, GPS component 67, a clock 84, and a display driver 82. The clock 84 indicates the current date and time to the microprocessor 76. For clarity of illustration, the clock 84 is shown as a separate component, but is preferably built into microprocessor 76. The display driver 82 operates under the control of the microprocessor 76 to display information on the display 64. The microprocessor 76 is preferably a PIC 16C6S processor that includes a universal asynchronous receiver transmitter (UART) 78. The UART 78 is for communicating with a modem 86 and a device interface 90. A CMOS switch 88 under the control of the microprocessor 76 alternately connects modem 86 and interface 90 to UART 78.

The wireless chip 66 is for exchanging data with the server 18 through a wireless communication network 24. The data includes script programs 40 which are received from the server 18 as well as responses 42 to queries, device measurements 44, script identification codes, the individual's and healthcare facility's unique identification code, and authentication codes that the chip 66 transmits to the server 18. The chip 66 is preferably a commercially available generic wireless transmitter-receiver embedded chip, although any suitable modem may be used. In an alternate embodiment of the invention, the chip 66 is suitably a WAP enabled, WLL enabled, 3G enabled, Bluetooth enabled, satellite telephone enabled, WiFi enabled embedded chip.

The device interface 90 is connected to the device jacks 68A, 68B, and 68C. The device interface 90 is for interfacing with monitoring device 28. The device interface 90 operates under the control of the microprocessor 76 to collect measurements 44 from the monitoring devices and to output the measurements to the microprocessor 76 for storage in the memory 80. In the preferred embodiment, the device interface 90 is a standard RS232 interface. For simplicity of illustration, only one device interface is shown in FIG. 4. However, in alternative embodiments, the apparatus 26 may include multiple device interfaces to accommodate monitoring devices 28 which have different connection standards.

GPS Component 67 is connected to the processor 76 allows the transmission of geographical localizer data to the system 16.

In alternate embodiments of the invention, the chip 66 may be a high speed cable modem, the device jacks 68A, 68B and 68C may be serial USB ports, and the communication network 24 a Local Area Network connected to the Internet. Such an embodiment will allow faster data transmission. In addition, the embodiment decreases the expenses that may be incurred in the installation of the system in healthcare and laboratory facilities that have preestablished network systems, In another embodiment, in addition to the above, monitoring device 28 is included in the casing 62 of apparatus 26 allowing a reduction in hardware and manufacturing costs.

Figure 5:
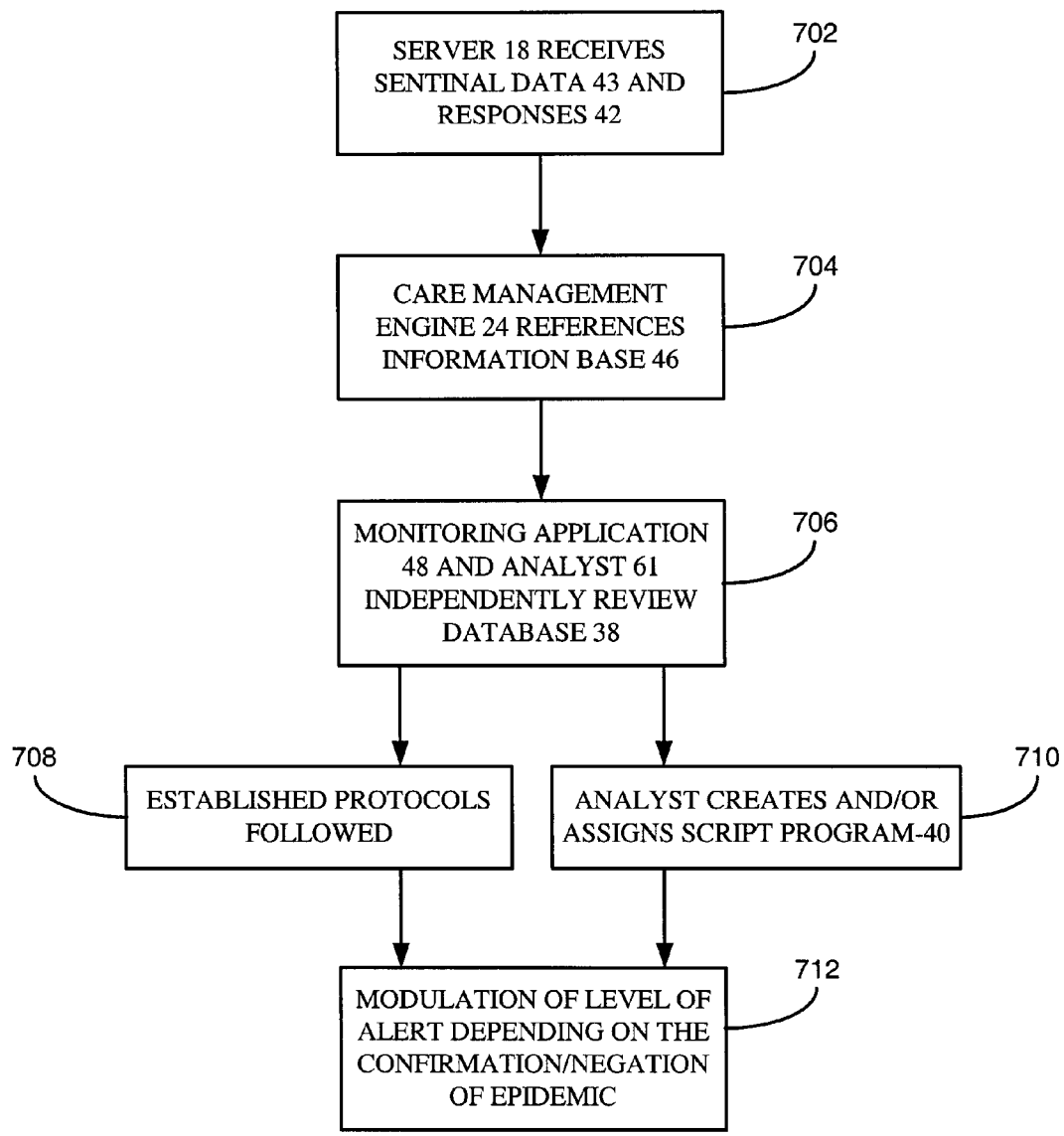
FIG. 5 illustrates the data collection process, according to the invention.

FIG. 5 illustrates the data collection and follow-up process, according to the invention. At a block 702, server 18 receives sentinel data 43 from the information system server 106, and responses 42 from individual 60 that include responses to queries and physiological measurements taken at a low frequency. The low frequency of queries and measurements is to ensure that the individual 60 remains in communication with the system on a regular basis, and is aware of the system. At a block 704, the monitoring application reviews the database 38 data continuously and automatically and independent manual review of data takes place by analyst 61. At a block 706, the analyst and/or the monitoring application 48 and its subcomponents determine that a combination of data in the database represents a "credible threat" in terms of a possible outbreak. In case the system 16 already has predefined protocols within protocols 53 on the procedure to be followed in case of the outbreak, the respective procedure is followed by the monitoring application at a block 708. Alternatively, at a block 710, the analyst 61 uses the script entry 56 and script assigns 57 screens to elicit more information about a possible outbreak. This is simultaneously accompanied by an increased frequency of data collection from the individual 60 who is living in adjacent areas, and a more regular analysis of all system data.

In this manner the system steps up from a passive collection of data, that is low burden on the individual and the healthcare system to a more active surveillance of data on the basis of the level of "threat" of an outbreak within the population. At a block 712, depending on the confirmation/negation of the presence of an outbreak, the level of alert, and of data collection may be further increased or brought back to the original levels. An advantage of the above is that the need for information and the burden posed to the healthcare system by the increased amount of collected and reportable information is balanced by the system process.

Two of the improvements on the BASIICS (Biothreat Active Surveillance Integrated Information and Communication System) application (public health surveillance) implemented by the system 16 are the following.

BASIICS for Quarantine:

Health Buddy (e.g., apparatus 26) is an ideal solution for monitoring a population that public health officers consider may be at risk of exposure to an infectious disease like SARS. (Severe Acute Respitory Syndrome) It allows frequent systematic monitoring and management by exception. The method of monitoring encourages patient compliance, but it does not guarantee it. In a situation like SARS, the people most at risk might be reluctant to comply with reporting symptoms because they could be worried about being quarantined.

Monitoring issues are addressed by combining a means of identifying the patient with the diagnostic test. The monitoring looks at DNA and various analytes in urine to ensure the identity of someone being monitored for drug use in a remote monitoring system. The present invention moves away from analytes and focuses on fingerprint identity and ensuring that there is a closed circuit with the patient analyte measurement.

The improved method for SARS measures temperature and validates that the person entering the data is the right person and is not cheating. The present invention includes a digital thermometer attached to Health Buddy. To ensure the identity of the person taking the temperature, a fingerprint reader may be built into Health Buddy. When the person is taking his temperature, he presses his index finger onto the fingerprint reader, identifying himself. The Health Buddy may also be able to measure the impedance through the circuit created from the digital thermometer to the mouth through the arm and the finger on the fingerprint reader. Based on the fingerprint and the impedance in the circuit it will be very hard to cheat the system.

BASIIS Intensity Sensitive to Threat Level:

Research showed at Stanford that personnel may unobtrusively collect data at triage for every patient coming through the Emergency Department. Many hospitals, however, believe that any additional data collection is too much of a burden. Other environments exist where intense monitoring may not be justified most of the time.

The BASIICS improvements generally allow the intensity of monitoring to be scaled to the threat level. When the threat is low (as determined by either prior data or a public health official), the survey runs once per shift. That way the user is kept aware of the system and still checks-in in a systematic way. When the threat level is elevated, the Health Buddy goes into a more intense mode, requesting data more than once per shift, at various levels including:

Once per hour or other interval.

Once per patient (in the case of an ER).

Once per patient with patient identification entry for the highest threat level.

The setting of the threat level in the server is communicated with the Health Buddy units in the field in several ways:

When the "first survey of the shift" is entered, Health Buddy dials in to send the data and retrieve new threat information. Health Buddy will be prompting the user for the "first survey of the shift" until the nurse checks in.

Threat levels, modes and survey content is sent to the Health Buddy by digital radio broadcast. Health Buddy dials in on the phone line to transmit responses to surveys (e.g., Broadcast downstream, dial-up for the back channel.) Therefore, all Health Buddy's are always current with the right info and mode.

A consumer device Health Buddy generally integrates the following elements:

Temperature measurement via a digital thermometer, or any other objective test.

Scripted survey for other data collection—GPS for location detection.

Optional identification methods for verifying who is doing the test (e.g., fingerprint).

Transmission of collected data to a server (e.g., wireless cell phone chip on board).

Ability to accept new program instructions or scripts wirelessly via digital broadcast or two way cell phone transmission).

The other embodiments may operate over Interactive TV, mobile device, and web as well as Health Buddy.

Back End Analytics:

Data feeds may be accepted from the following sources:

Over the counter retail sales of pharmacy nationwide to identify a spike in sales of any drug that might indicate an outbreak.

Chief complaint data from hospital emergency departments, captured through existing web based systems or through Health Buddy. The intensity of data collection depends on the alert level. When there is low alert, there is still an interaction but it is less frequent and such an interaction may be referred to as a "continuous training".

Data from in-home monitoring.

From vulnerable populations already in some kind of monitoring, like elderly patients with heart failure or AIDS patients with compromised immune systems. The vulnerable populations are the "canary" in the mine. Unusual incidence of symptoms in a vulnerable population can be an early detector of other things coming.

From populations determined by public health to be at risk and are in some kind of quarantine situation.

The analytics engine will look at the combination of pharmacy, hospital, and home data in a region or metro area to determine if there is suspicion that needs to be investigated further. When suspicion is raised, the system will send out more detailed and additional questions to the participants.

A mission of BASIICS may be to save lives by improving the public health training, surveillance and response infrastructure for detecting and mitigating biological threats. A strategy may be to improve slow, passive reporting with active disease surveillance. Another strategy may replace static paper forms and faxes with survey technologies that may adapt to new information. Still another strategy may aggregate consistent data for real-time analysis across local and regional jurisdictions. Another strategy may adapt the intensity of the monitoring and intervention to the threat level.

Referring to FIG. 6, a table of a BASIICS model is shown. The model generally comprises a comprehensive surveillance, training and intervention model. Rows of description, pharmacy, hospital and home elements are shown relative to (i) low threat, (ii) suspicion or high risk event and (iii) confirmed threat, outbreak or attack threat statuses.

Figure 7:
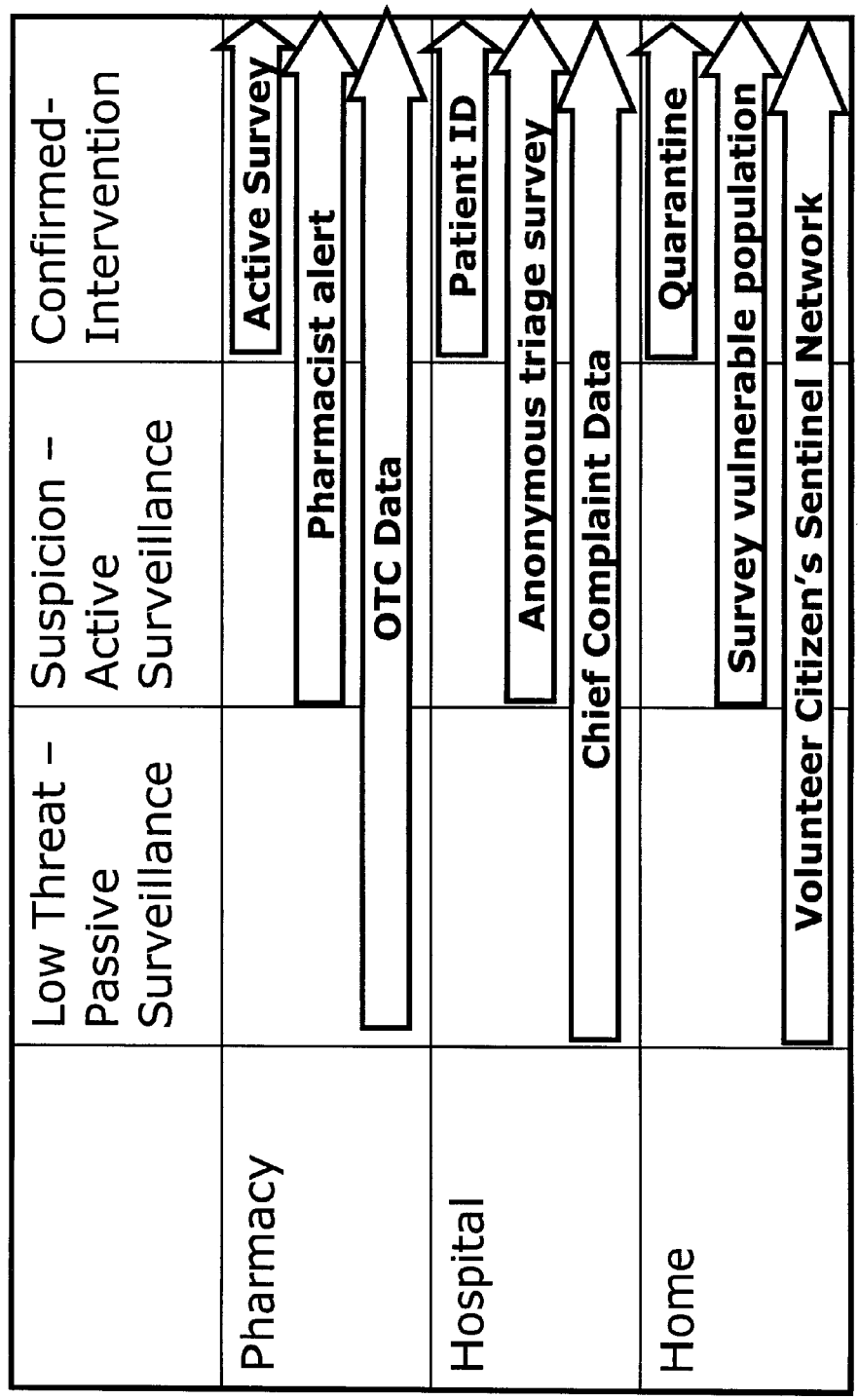
FIG. 7 is a diagram of step-up intensity based on a threat level.

Referring to FIG. 7, a diagram of step-up intensity based on the threat level is shown. The row of pharmacy, hospital and home elements are shown relative to (i) low threat—passive surveillance, (ii) suspicion—active surveillance and (iii) confirmed—intervention actions.

Figure 8:
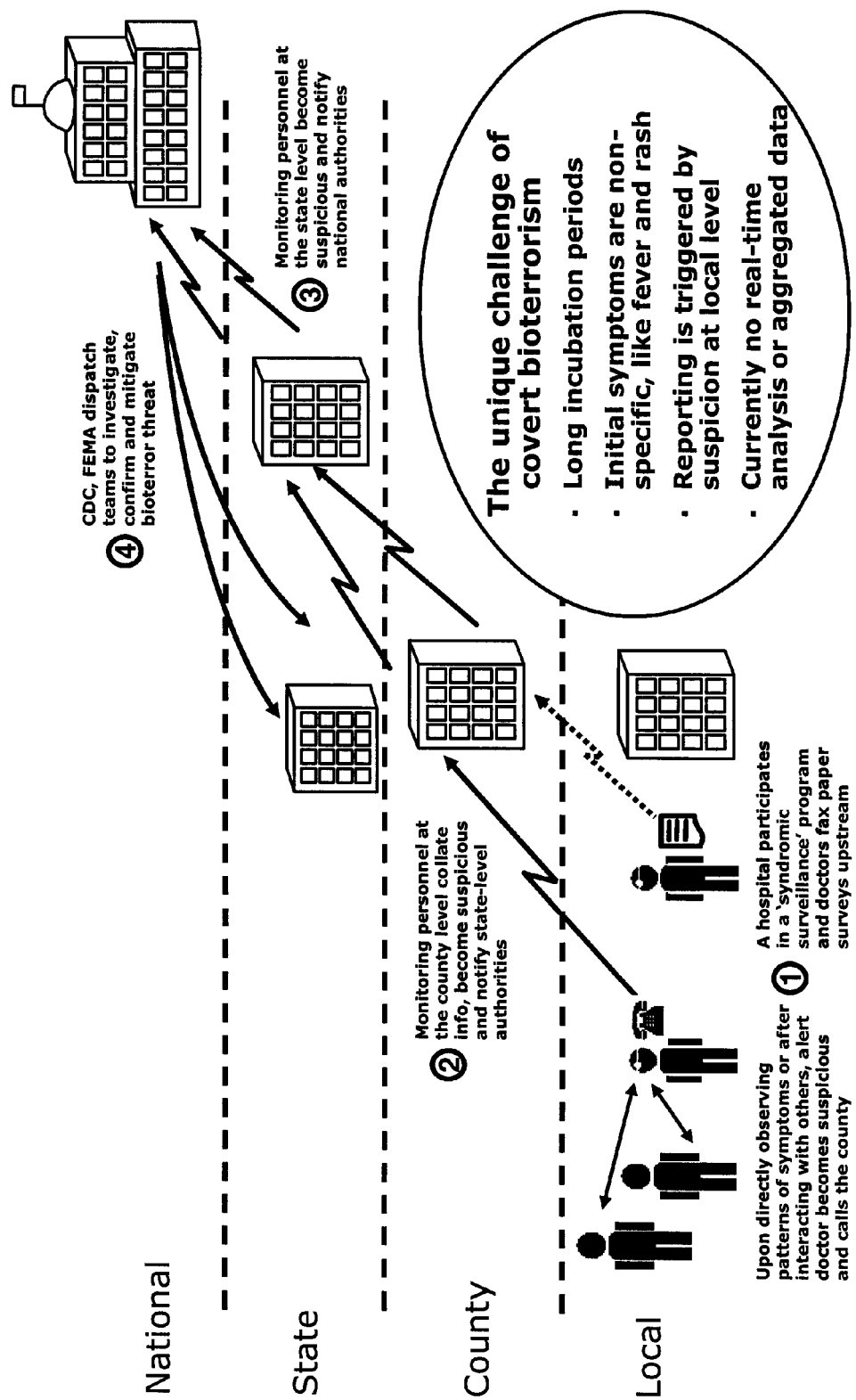
FIG. 8 is a block diagram of a reporting process.

Referring to FIG. 8, a block diagram of a reporting process is shown. The process (or method) generally includes activities at a local level, a county level, a state level and a national level. At the local level, doctors and/or hospitals may notify the county level of suspicious activity. At the county level, monitoring personnel may collate information and notify the state level, if appropriate. Monitoring personnel at the state level generally monitor the county level information and notify the national level when appropriate. At the national level the Center for Disease Control (CDC) and/or the Federal Emergency Management Agency (FEMA) may dispatch teams to investigate the reports. Some of the unique challenges of covert bioterrorism type activity may include long incubation periods, non-specific initial symptoms like fever and rash, reporting may be triggered by suspicion at local level and no real-time analysis or aggregated data is currently available.

Figure 9:
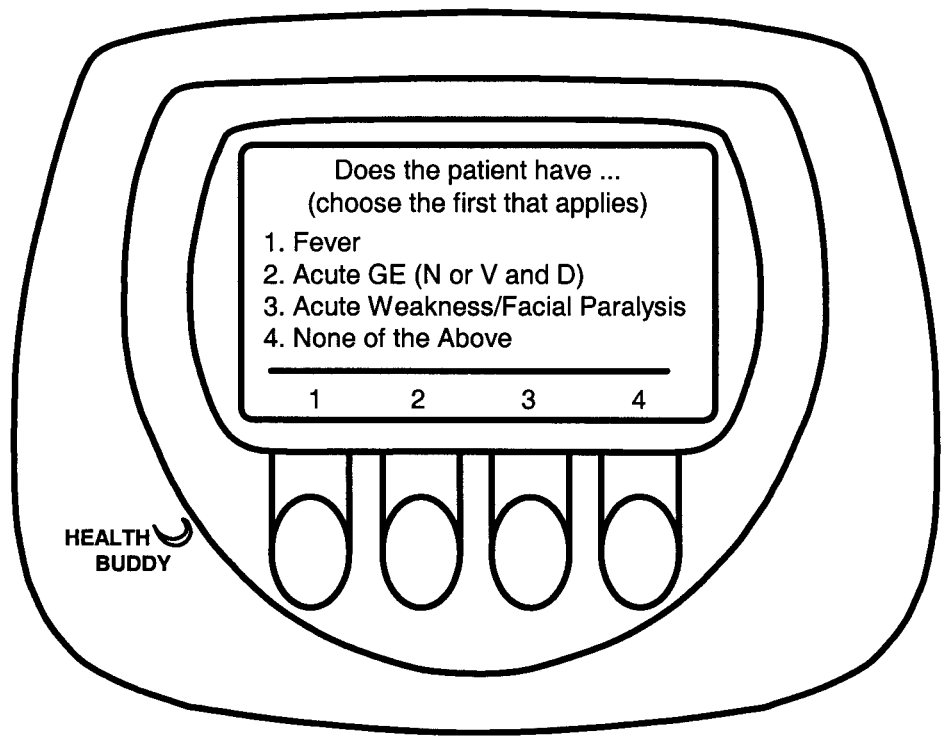
FIG. 9 is a diagram of a front view of a Health Buddy.

Referring to FIG. 9, a diagram of a front view of a Health Buddy is shown. Low burden field data capture may be achieved using the Health Buddy. For example, front-line medical professionals may report data simply by pushing buttons on low burden desktop devices. The Health Buddy may be used for training and surveillance at home, hospitals and/or pharmacies. Furthermore, consolidated structured syndromic data may be analyzed statistically and in real-time.

Referring to FIG. 10, diagram showing an example set of screens on a Health Buddy is shown. The screens generally illustrate a dynamic survey capability using the Health Buddy. In a first screen, the patient may be queried for specific symptoms. An interactive survey with conditional logic enables follow-up questions based on risk factors, as shown in the middle screen. The surveys may be refined quickly in response to changing conditions and intelligence, as shown in the bottom screen.

Figure 11:
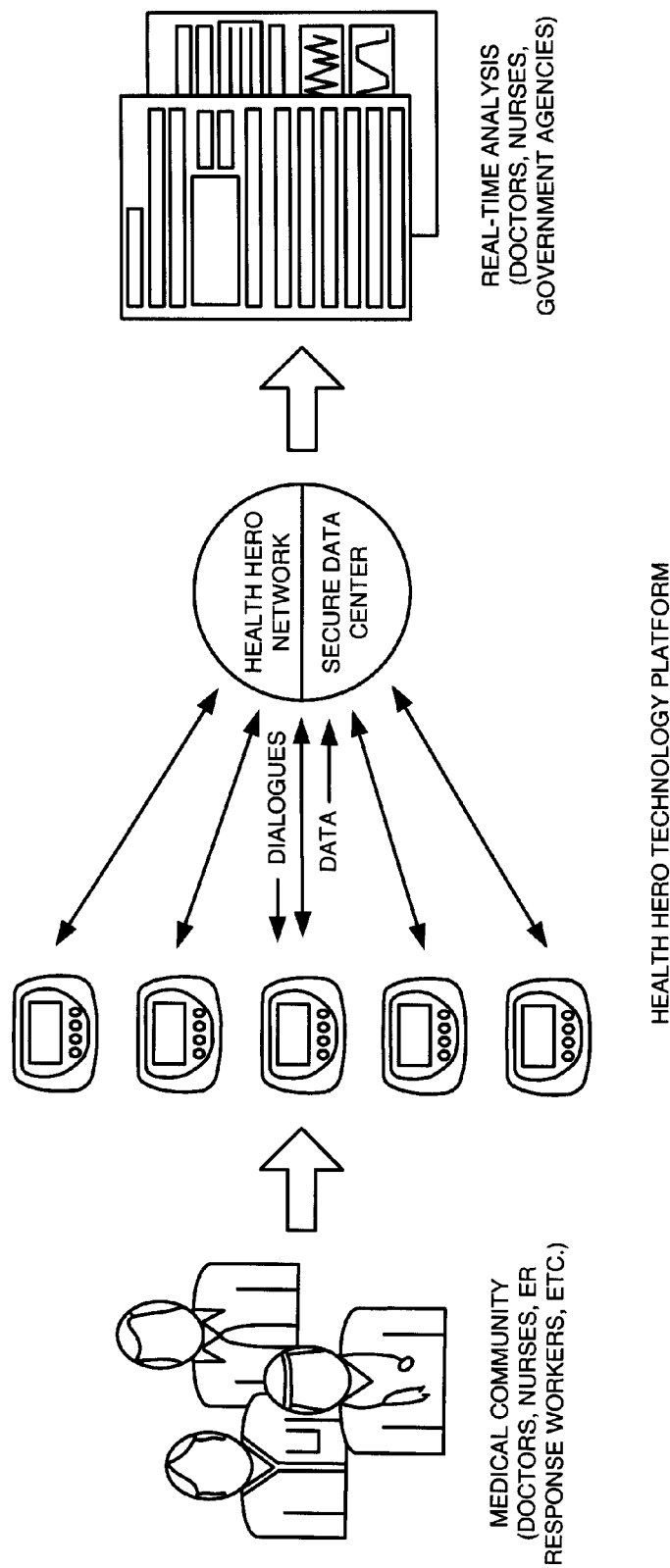
FIG. 11 is a diagram of a data flow for an active disease surveillance.

Referring to FIG. 11, a diagram of a data flow for an active disease surveillance is shown. The surveillance may be performed using a Health Hero network platform. The platform generally comprises the medical community and the Health Buddies. The medical community may interact with the Health Buddies. The Health Buddies generally exchange data and dialogues with a secure data center via a network. The secure data center may perform real-time analysis for doctors, researchers and/or government agencies.

Referring to FIG. 12, a table comparing the Health Hero network to a conventional process is shown. The table generally lists several example criteria in a left column. A middle column explains how each criteria is handled by the conventional process. A right column explains how the Health Hero network performs for each of the criteria.

Figure 13:
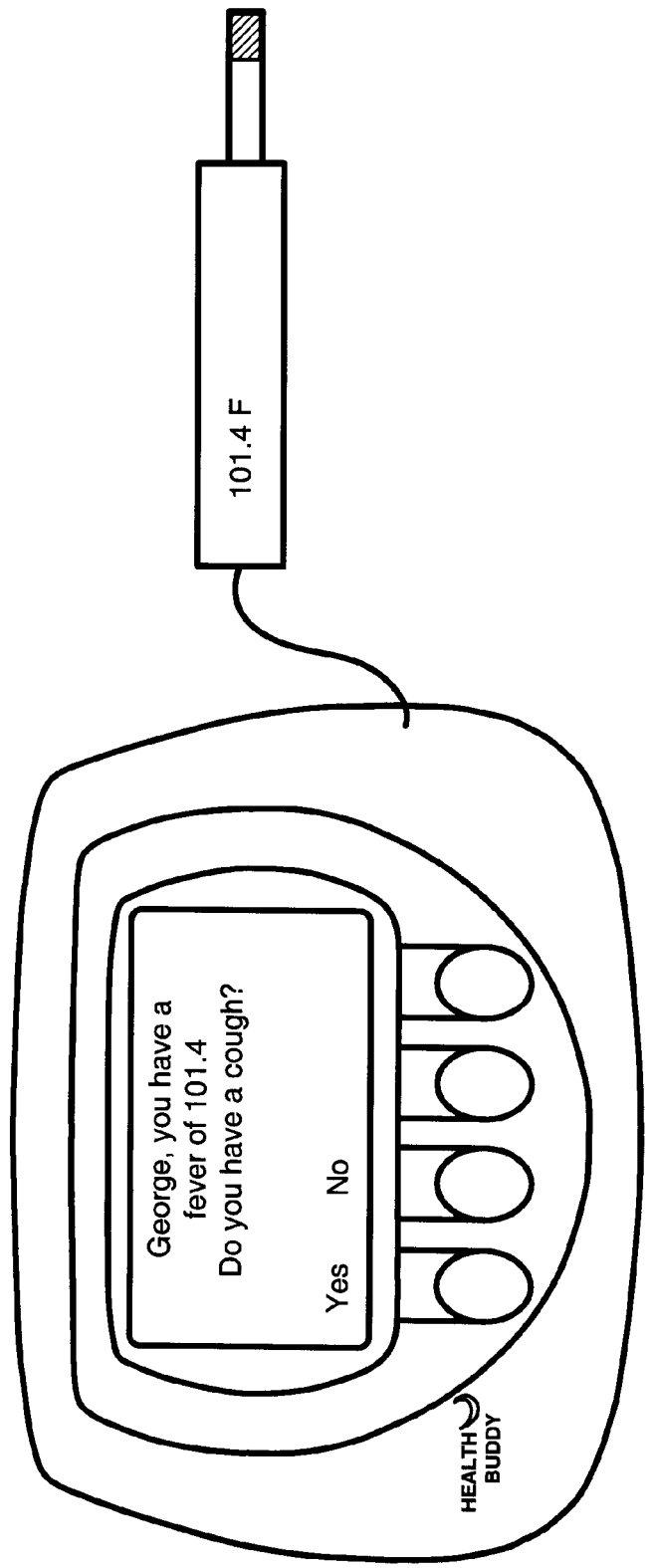
FIG. 13 is a diagram of a Health Buddy coupled to a first sensor.

Referring to FIG. 13, a diagram of a Health Buddy coupled to a first sensor is shown. The first sensor may be implemented as a thermometer. Volunteers in a Citizen Sentinel Network may report symptoms measured using the sensor anonymously on a regular basis. Vulnerable, chronically ill, at risk, exposed and/or quarantined populations may be monitored frequently and automatically using the sensor and the Health Buddy. Thereafter, consolidated structured syndromic data may be analyzed statistically and in real-time.

Figure 14:
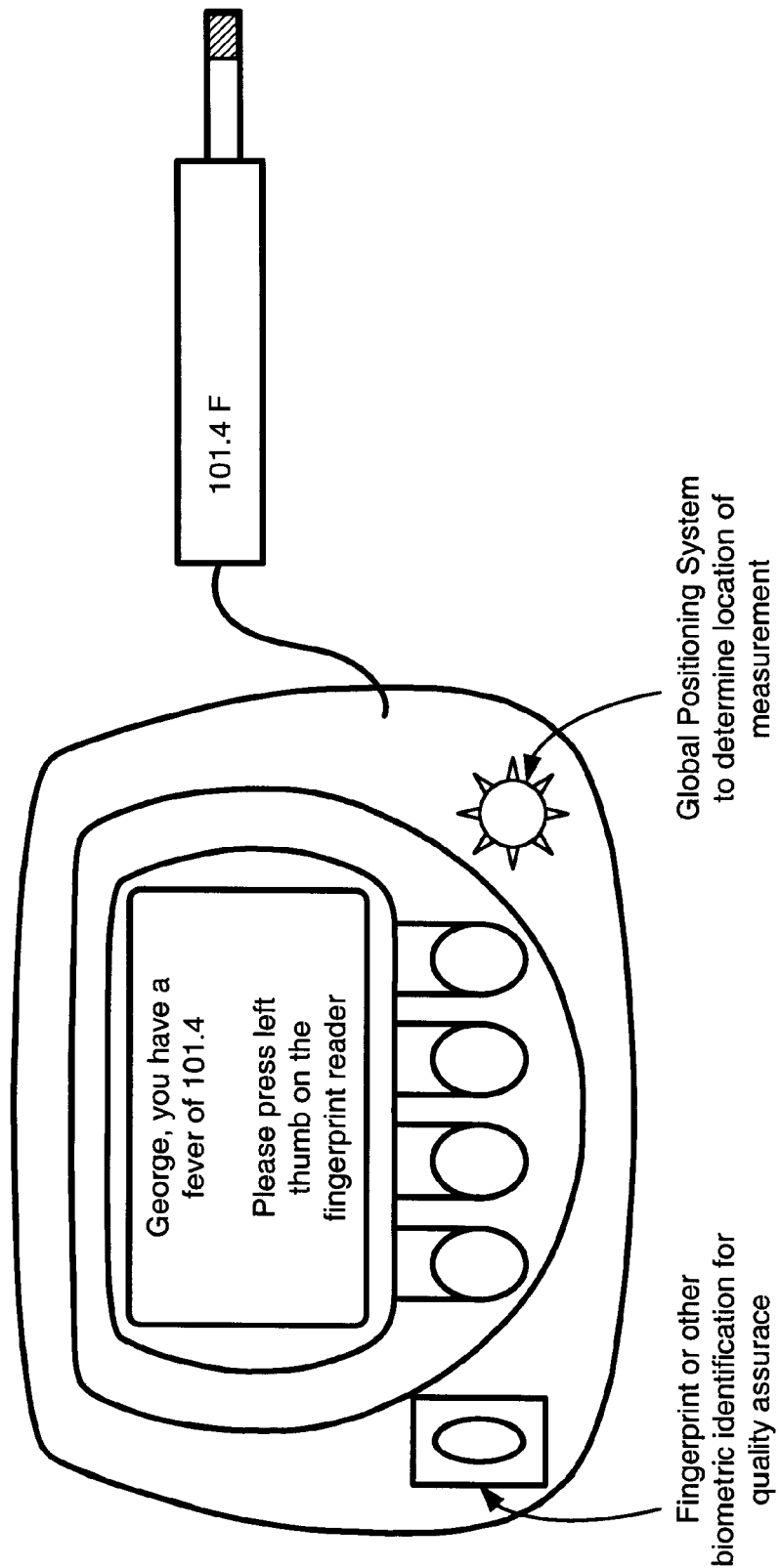
FIG. 14 is a diagram of a Health Buddy coupled to a second sensor.

Referring to FIG. 14, a diagram of a Health Buddy coupled to a second sensor is shown. The second sensor may be implemented as a fingerprint identification device or another biometric identification device. The second sensor may be used for quality assurance. A Global Positioning System (GPS) receiver 67 may be incorporated in the Health Buddy to determine a location of the measurements. Furthermore, a time-stamped location, identity and measurement packet may be transmitted to the data center via wireless data transmission.

Figure 15:
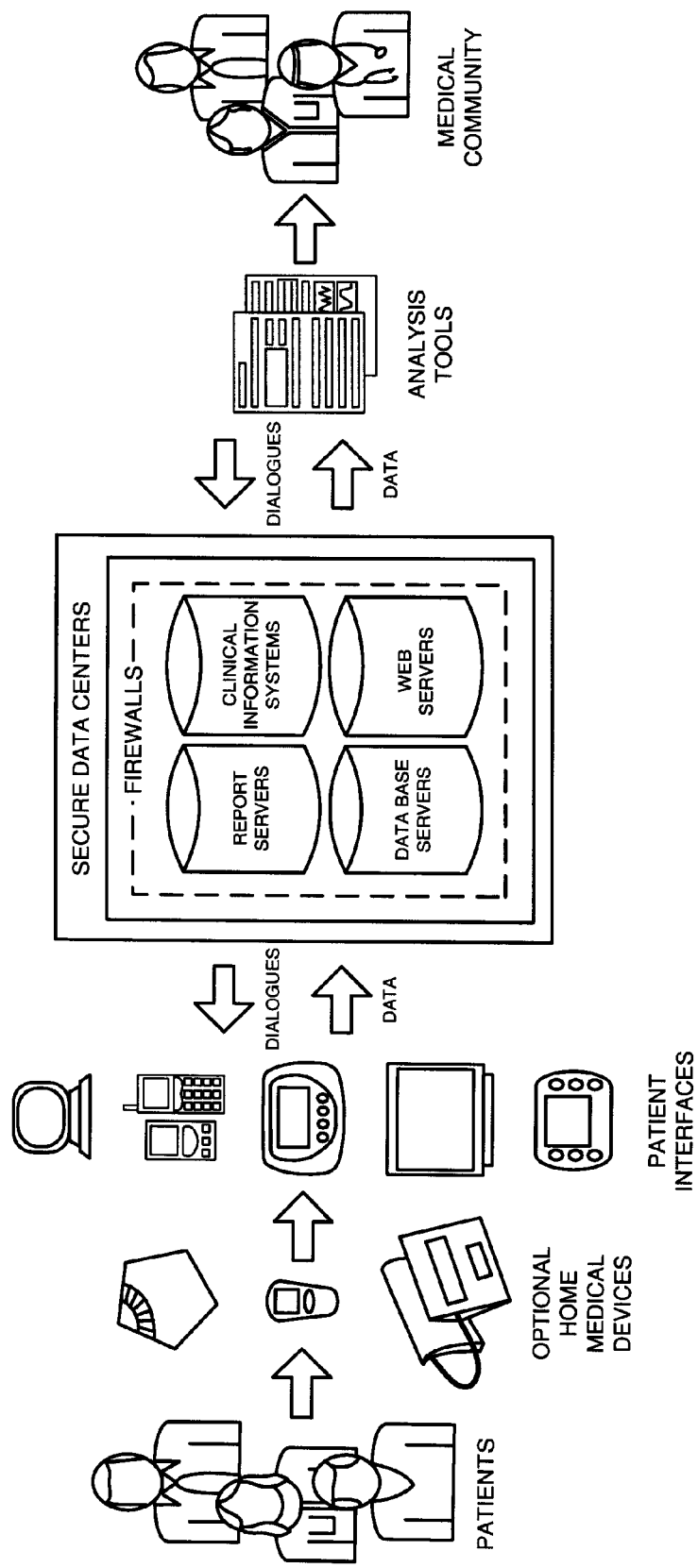
FIG. 15 is a diagram of example technologies and formats that may be used in the monitoring.

Referring to FIG. 15, a diagram of example technologies and formats that may be used in the monitoring is shown. Individuals may interact with the secure data centers through the various forms of Health Buddies (e.g., patient interfaces) either directly and/or through a variety of optional home medical devices. The secure data centers may provide analysis tools to interact with the medical community.

Figure 16:
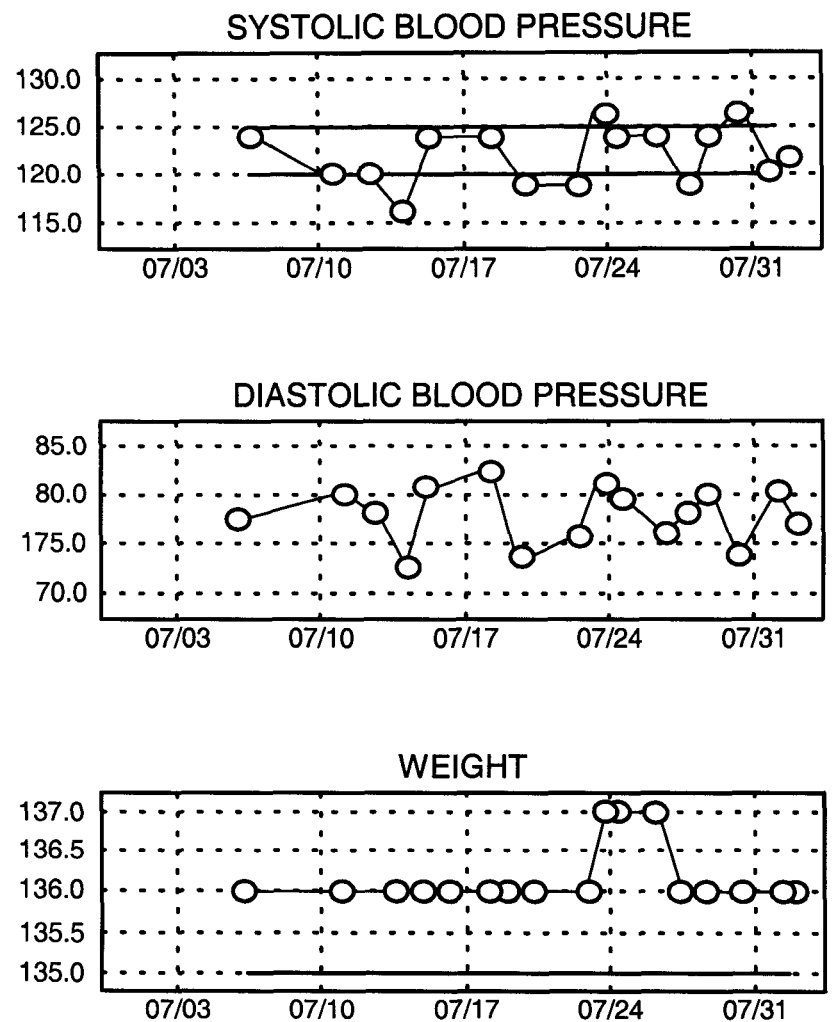
FIG. 16 is a schematic block diagram of example patient profile and patient summaries.

Referring to FIG. 16, a schematic block diagram of example patient profile, shown in further detail in FIG. 16(a), and patient summaries, shown in further detail in FIG. 16(b), is shown. The medical community users may use the analysis tools for threat detection and management.

Referring to FIG. 17, a diagram of example interactive dialogues is shown. In the example, public health questions may be added to existing disease management queries.

The monitoring system generally provides biometric patient identification, GPS location detection, programming of scripted surveys based on latest threat information via digital broadcast and wireless data uploaded to central server. An analysis engine may analyze overlay of over the counter medications, chief complaints and/or home data to confirm outbreak or other anomalies. A threat level may be increased upon suspicion of a problem to actively collect enhanced data.

The monitoring system may include several options. For example, the Health Buddy may communicate with a digital thermometer plugged in via a BuddyLink. In another example, an integrated digital thermometer and survey capability may be provided in a wireless dedicated device. Furthermore, survey and data may be collection from consumer electronics platforms, such as mobile phones and personal digital assistant (PDA) applications. Digital interactive television application may be used for data collection. Satellite digital broadcasts with back-channel communications may be used for immediate national coverage. Furthermore, web applications may be integrated and/or accessed via web portals (e.g., Yahoo, MicroSoft Network (MSN) and America On Line (AOL)).

The present invention may provide several benefits compared with conventional approaches. For example, the Health Hero Network may give public health officials the ability to actively survey and analyze data from thousands of medical sites, pharmacies and homes.

Patterns may be identified at regional, state, national level with real-time data analysis. Health officials may dynamically probe deeper and ask new questions based on new information. Furthermore, the low-burden technology generally fits into existing health care processes, with intensity of monitoring that scales based on the threat level.

What is claimed is:

1. A computer implemented method for monitoring a plurality of individuals located across a regional, state, or national geographic area using a server executing instructions stored on a computer readable medium, the instructions comprising:

(A) receiving, with the server, health-related data corresponding to one or more health conditions of said plurality of individuals from a respective device of a plurality of devices associated with said plurality of individuals and configured to produce said health-related data by (i) measuring one or more physiological parameters related to said one or more health conditions and (ii) receiving responses to one or more queries presented to said plurality of individuals, wherein said plurality of devices are (i) remotely located from said server, (ii) in communication with said server via a communications network, (iii) configured to generate data corresponding to a geographical location of each respective device of said plurality of devices, and (iv) configured to transmit said health-related data and said data corresponding to a geographical location of each respective device of said plurality of devices to said server;

(B) highlighting (i) a population and (ii) a geographic region at risk of exposure to a disease by analyzing, with the server, said health-related data and said data corresponding to said geographical location of each respective device of said plurality of devices;

(C) generating, with the server, one or more reports based on said health-related data and said data corresponding to said geographical location of each respective device of said plurality of devices; and (D) scaling, with the server, a level of surveillance among said plurality of individuals using the plurality of devices in response to a change in a threat level of said disease.

2. The method according to claim 1, further comprising the step of:
generating, with the server, a visualization of said health-related data in response to said data corresponding to said geographical location of each respective device of said plurality of devices received from said devices.

3. The method according to claim 2, further comprising the steps of:
generating, with the server, one or more surveys for one or more symptoms in response to said health-related data suggesting one or more outbreaks of said disease; and
transmitting, with the server, said surveys only to devices in proximity to one or more of said locations associated with said outbreaks based on said data corresponding to said geographical location of each respective device of said plurality of devices.

4. The method according to claim 1, further comprising the steps of:
storing one or more programs in said server; and
transmitting said programs to one or more of said plurality of devices to convey one or more messages to one or more of said plurality of individuals.

5. The method according to claim 1, wherein said health-related data and said data corresponding to said geographical location of each respective device of said plurality of devices comprises sentinel data from a group of said individuals likely to catch said disease.

6. The method according to claim 1, wherein said one or more health conditions comprise at least one of (i) one or more physiological conditions and (ii) one or more symptoms.

7. The method according to claim 1, wherein said health-related data comprises one or more environmental variables.

8. The method according to claim 1, wherein the method further comprises:
generating, with the server, one or more surveys in response to said health-related data and said data corresponding to said geographical location of each respective device of said plurality of devices when said health-related data and said data corresponding to said geographical location of each respective device of said plurality of devices suggest a link between said disease and at least one of said one or more health conditions among said plurality of individuals.

9. The method according to claim 5, wherein the method further comprises:
transmitting said surveys to said plurality of devices in said highlighted population and said highlighted geographic region.

10. The method according to claim 1, wherein said geographical location is generated by a global positioning system (GPS) located in each of said devices.

11. The method according to claim 1, wherein said data corresponding to said geographical location includes a time-stamped geographical location.

* * * * *